(12) United States Patent
Buder et al.

(10) Patent No.: US 8,002,949 B2
(45) Date of Patent: Aug. 23, 2011

(54) TISSUE PRODUCTS CONTAINING SOFTNESS

(75) Inventors: Philip Buder, Mississauga (CA); Vincent Denis Landry, Rosemere (CA); Charles William Alexander Stewart, Burnaby (CA); Jose Enrique Castell Perez, Carabobo (VE); Richard Hector Gendron, Gatineau (CA); Marc Joseph Gilles Desaulniers, Repentigny (CA)

(73) Assignee: Kruger Products L.P., Mississauga, ON (CA)

( * ) Notice: Subject to any disclaimer, the term of this patent is extended or adjusted under 35 U.S.C. 154(b) by 14 days.

(21) Appl. No.: 12/587,376

(22) Filed: Oct. 6, 2009

(65) Prior Publication Data
US 2010/0089540 A1    Apr. 15, 2010

Related U.S. Application Data

(63) Continuation of application No. 10/297,053, filed as application No. PCT/CA02/00475 on Apr. 8, 2002, now Pat. No. 7,597,780.

(60) Provisional application No. 60/282,143, filed on Apr. 9, 2001.

(51) Int. Cl.
*D21H 17/33* (2006.01)
*D21H 21/14* (2006.01)
*D21H 23/00* (2006.01)

(52) U.S. Cl. ............ 162/164.4; 162/123; 162/158; 162/164.6; 162/179; 162/180; 162/184; 106/287.11; 106/287.14

(58) Field of Classification Search ............ 162/123, 162/158, 164.4, 164.6, 179, 180, 184; 106/287.11, 106/287.14
See application file for complete search history.

(56) References Cited

U.S. PATENT DOCUMENTS

| | | | | |
|---|---|---|---|---|
| 5,059,282 | A * | 10/1991 | Ampulski et al. | 162/111 |
| 5,164,046 | A * | 11/1992 | Ampulski et al. | 162/111 |
| 5,552,020 | A * | 9/1996 | Smith et al. | 162/164.4 |
| 5,573,637 | A * | 11/1996 | Ampulski et al. | 162/112 |
| 5,679,218 | A * | 10/1997 | Vinson et al. | 162/109 |
| 5,904,810 | A * | 5/1999 | Schroeder et al. | 162/111 |
| 5,908,707 | A * | 6/1999 | Cabell et al. | 428/537.5 |
| 6,136,215 | A * | 10/2000 | Evans et al. | 252/8.81 |
| 6,432,270 | B1 * | 8/2002 | Liu et al. | 162/164.4 |
| 6,528,121 | B2 * | 3/2003 | Ona et al. | 427/387 |
| 2004/0115155 | A1 * | 6/2004 | Salvador et al. | 424/70.13 |

FOREIGN PATENT DOCUMENTS
WO    WO 9604424 A1 *   2/1996

OTHER PUBLICATIONS

International Cosmetic Ingredient Dictionary and Handbook Ninth Ed. vol. 1, 2002; Cover and pp. 2138, 185, 186 and 1188.

* cited by examiner

*Primary Examiner* — Matthew J Daniels
*Assistant Examiner* — Dennis Cordray
(74) *Attorney, Agent, or Firm* — Margaret J. McLaren; McLaren Legal Services

(57) ABSTRACT

A composition for cellulostic fibers containing amino silicone to impart improved hand feel. The composition may be included in a lotion applied to tissue paper and may include a hydrophilic softener. A carrier for trace substances, fragrances, vitamin E, aloes and colouring agents may also be used. Such carrier may comprise microcapsules.

11 Claims, 26 Drawing Sheets

MIXTURES PREPARED FOR LOTIONIZING TRIALS

| | | Item Code = | Am<br>DowCorning<br>Dc 2-8040 | Sur<br>DowCorning<br>DC-190 | Soh<br>DowCorning<br>DC Q1-3563 | Sil<br>DowCorning<br>Z-6040 | Mo<br>PetroCanada<br>Purity WO-15 | 802<br>Witco<br>PA-802 | W<br>IGI Waxes<br>Micro 5702 | Pg<br>Ashland<br>Propyl-Glycol | PPG<br>Goldschmidt<br>PPG-11 Stearyl |
|---|---|---|---|---|---|---|---|---|---|---|---|
| | | Supplier =<br>Supplier Item=<br>Supplied Kg =<br>Inventory Kg=<br>Ordered Kg = | 190<br>190 | 18.1<br>18.1 | 54.3<br>54.3 | 18.1<br>18.1 | 80L<br>68.0 | 17.5*<br>32.5*<br>15* | 1.36<br>1.36 | 0<br>180 | 0<br>0<br>180 |
| Direction<br>Action | Formula by<br>Item Codes | No. of<br>Pails | Quantity<br>Kg | PROFILE OF INGREDIENTS BY WEIGHT PERCENTAGE OF FORMULA | | | | | | | | |
| Repack | DC 2-8040 | 2 | 40 | 100% | | | | | | | | |
| Blend | Am75/Sur25 | 1 | 10 | 75.0% | 25.0% | | | | | | | |
| Blend | Am25/Sur75 | 1 | 10 | 25.0% | 75.0% | | | | | | | |
| Residual | DC-190 | 1 | 5 | | 100% | | | | | | | |
| Blend | Am75/Soh25 | 1 | 10 | 75.0% | | 25.0% | | | | | | |
| Blend | Am25/Soh75 | 1 | 10 | 25.0% | | 75.0% | | | | | | |
| As Is | DC Q1-3563 | 1 | 20 | | | 100% | | | | | | |
| Blend | Sur10/Mo90 | 1 | 10 | | 10.0% | | | 90.0% | | | | |
| Blend | Sur40/Mo60 | 1 | 10 | | 40.0% | | | 60.0% | | | | |
| Blend | Am75/Mo25 | 1 | 20 | 75.0% | | | | 25.0% | | | | |
| Blend | Am25/Mo75 | 1 | 20 | 25.0% | | | | 75.0% | | | | |
| As Is | Purity WO-15 | 1 | 20 | | | | | 100% | | | | |
| Blend | SPL-802-W.1 | 1 | 10 | | | | | | 95.0% | 5.0% | | |
| Blend | SPL-802-W.2 | 1 | 10 | | | | | | 70.0% | 5.0% | 1.0% | |
| Blend | SPL-802-W.3 | 1 | 10 | | | | | | | 5.0% | 3.8% | |
| | Super Mix | 1 | 10 | 91.2% | 18.8% | 18.8% | | 18.8% | | | | |
| | AM60/PPG40 | 1 | 10 | 60.0% | | | | | | | | 40.0% |

FIG. 4

| Formula by Item Codes | No. of Pails | Viscosity cPs @ 25C | Surf. Tension Dynes/cm |
|---|---|---|---|
| DC 2-8040 | 2 | 4,800 | 22.0 |
| Am75/Sur25 | 1 | 19,300 | 25.1 |
| Am25/Sur75 | 1 | 4,500 | 23.9 |
| DC-190 | 1 | 1,560 | 22.2 |
| Am75/Soh25 | 1 | 2,925 | 20.1 |
| Am25/Soh75 | 1 | 325 | 21.1 |
| DC Q1-3563 | 1 | 75 | 21.3 |
| Sur10/Mo90 | 1 | 25 | 22.9 |
| Sur40/Mo60 | 1 | 88 | 23.6 |
| Am75/Mo25 | 1 | 3,200 | 20.5 |
| Am25/Mo75 | 1 | 50 | 20.7 |
| Purity WO-15 | 1 | 13 | 29.8 |
| SPL-802-W.1 | 1 | 5,700@35C | 29.0@72C |
| SPL-802-W.2 | 1 | 2,400@23C | 21.9@35C |
| SPL-802-W.3 | 1 | 7,500@24C | 20.3@35C |
| Super Mix | 1 | n/t | n/t |
| AM60/PPG40 | 1 | 580 | ~26 |

FIG. 5

TRIAL TESTING 23 LOTIONED VARIANTS OF 3PLY SCOTTIES SUPREME EX HUS

| PRODUCT FORMAT | | 100 | 101 | 102 | 103 | 104 | 105 | 106 |
|---|---|---|---|---|---|---|---|---|
| FORMULA NAME | | SC SPRM PLAIN | ZQuat 0.8g eat 0.8gs | Z-Q 0.5 gs eat 0.5 gs | Z-Q 0.7 gs eat 0.7gsm | SOH100 | Z-Quat 25 EtOH 75% | AM60/PPG PPG40% |
| Comment | | 0 | | | | 60 | | 115 |
| Measured DOSE of Lotion on Web^* | Avg Kg/MT | Nil | Dryer 100C | No Heat | No Heat | Low | No Heat | Low |
| Comment on Dryer Temperature or Lotion Dose | | | | | | | | |
| PRODUCT ATTRIBUTES | | | | | | | | |
| BASIS WEIGHT | Lb / Rm | 29.1 | 30.9 | 29.6 | 30 | 31.3 | 28.1 | 30.9 |
| BASIS WEIGHT | g /-sq.m | 47.4 | 50.3 | 48.2 | 48.8 | 50.9 | 45.7 | 50.3 |
| BULK-FEDERAL (24sh) | x 0.001" | 274 | 252 | 263 | 264 | 244 | 246 | 246 |
| BULK-THWING (12sh) MICRONS | uM | 3,831 | 3,632 | 3,662 | 3,702 | 3,457 | 3,591 | 3,410 |
| MD STRETCH% | % | 14.2 | 10.9 | 11.6 | 10.1 | 8.3 | 9.7 | 9.5 |
| CD STRETCH% | % | 7.2 | 6.9 | 7.0 | 5.9 | 4.9 | 7.0 | 5.8 |
| MD TENSILE DRY | Oz / Inch | 20.4 | 14.4 | 14.6 | 12.4 | 15.0 | 16.8 | 13.6 |
| CD TENSILE DRY | Oz / Inch | 7.0 | 6.8 | 6.1 | 5.1 | 5.0 | 5.6 | 5.2 |
| MD WET TENSILE (nat) | Oz / Inch | 9.9 | 6.8 | 7.1 | 8.0 | 7.3 | 6.2 | 7.7 |
| CD WET TENSILE (nat) | Oz / Inch | 4.1 | 3.8 | 3.3 | 3.6 | 3.8 | 3.0 | 3.8 |
| MD WET TENSILE (art) | Oz / Inch | 10.0 | 8.2 | 7.5 | 8.8 | 8.8 | 7.6 | 7.2 |
| CD WET TENSILE (art) | Oz / Inch | 4.7 | 5.0 | 3.3 | 3.5 | 3.5 | 2.7 | 3.1 |
| ABSB. 1-PLY SEC./.1cc | Sec. | | | | | | | |
| ABSB. 1-PLY SEC./.01cc | Sec. | 1 | 1 | 1 | 1 | 1 | 1 | 1 |
| BRIGHTNESS - GE @ 452 nm | % Refl. | 85.7 | 83.4 | 84.7 | 84.1 | 84.7 | 85.2 | 83.8 |
| CLEANLINESS FACTOR | ww | | | | | | | |
| HANDFEEL by NW QC Techs. | Average | 93 | 98 | 93 | 92 | 92 | 98 | 103 |
| SOFTNESS (Handfeel by WWSM) | | 0 | 96 | n/a | n/a | 91 | 94 | 112 |

FIG. 7a-1

TRIAL TESTING 23 LOTIONED VARIANTS OF 3PLY SCOTTIES SUPREME EX HUS

| | 107 | 108 | 109 | 110 | 111 | 112 | 113 | 114 | 115 |
|---|---|---|---|---|---|---|---|---|---|
| | P-637 5% Water 95% | AM60/PPG PPG40% | SOH100 | P1510 10% Water 90% | SC SPRM PLAIN | Z-Quat 50 EtOH 50% | AM25/SOH SOH75% | SC SPRM PLAIN | AM25/SOH SOH75% |
| | | 91 | 64 | | 0 | | 131 | 0 | 54 |
| 142C | | High | High | Low | No Heat | No Heat | High | Nil | Low |
| | 28.2 | 30.1 | 30 | 28.3 | 32.6 | 30.9 | 32.3 | 28.3 | 30.2 |
| | 45.9 | 49.0 | 48.8 | 46.1 | 53.1 | 50.3 | 52.6 | 46.1 | 49.2 |
| | 244 | 236 | 254 | 250 | 270 | 250 | 237 | 274 | 266 |
| | 3,436 | 3,338 | 3,558 | 3,543 | 3,724 | 348 | 3,310 | 3,805 | 3,776 |
| | 9.0 | 7.7 | 10,15.8 | 9.5 | 13.4 | 12.9 | 7.6 | 14.1 | 11.4 |
| | 6.5 | 6.0 | 14.8 | 6.7 | 6.9 | 6.3 | 4.1 | 5.6 | 5.6 |
| | 17.0 | 14.4 | 5.1 | 17.8 | 18.2 | 15.6 | 12.7 | 18.1 | 16.0 |
| | 6.3 | 4.9 | 7.9 | 6.6 | 6.8 | 6.2 | 4.8 | 7.1 | 6.1 |
| | 8.8 | 5.0 | 3.2 | | 6.8 | 5.8 | will not absorb | 7.7 | will not absorb |
| | 3.1 | 2.5 | diff | | 3.0 | 3.0 | | 3.3 | |
| | 7.3 | diff | to abs | 7.1 | 9.9 | 8.4 | will not absorb | 9.3 | will not absorb |
| | 3.2 | to abs | | | 3.6 | 3.5 | | 4.5 | |
| | 7 | 2 | ** | | 1 | 1 | 29 | 1 | ** |
| | 85 | 83.2 | 83.9 | 85.5 | 85.6 | 85.6 | 83.1 | 85.7 | 84.6 |
| | 105 | 103 | 103 | 98 | 90 | 93 | 102 | 98 | 102 |
| | n/t | 110 | 100 | n/t | 88 | 99 | 111 | 92 | 106 |

FIG. 7a-2

TRIAL TESTING 23 LOTIONED VARIANTS OF 3PLY SCOTTIES SUPREME EX HUS

| | 116 | 117 | 118 | 119 | 120 | 121 | 122 | 123 |
|---|---|---|---|---|---|---|---|---|
| | SUPER MI Blend 126 High | SUPER MI Blend 55 Low | Z-QUAT 50 EtOH 50% No Heat | SOLUSOF Neat Flexo 39 115C | SOLUSOF Neat Spray 78 160C | AM25/MO7 MO 75% 37 162C | TEGO FS4 Neat 42 159C | P-637 5% Water 95% 154C |
| | 31.9 | 30.7 | 28.8 | 28.5 | 29.0 | 29.5 | 28.1 | 28.3 |
| | 51.9 | 50.0 | 46.9 | 46.4 | 47.2 | 48.0 | 45.7 | 46.1 |
| | 240 | 264 | 264 | 250 | 262 | 260 | 258 | 278 |
| | 3,76 | 3,723 | 2,698 | 3,490 | 3,735 | 3,606 | 3,699 | 3,589 |
| | 7.7 | 9.6 | 12.6 | 10.1 | 8.7 | 9.7 | 12.7 | 12.2 |
| | 4.2 | 4.5 | 5.5 | 5.2 | 6.1 | 6.0 | 5.0 | 5.7 |
| | 13.7 | 14.0 | 17.5 | 17.0 | 12.3 | 15.6 | 15.8 | 18.3 |
| | 4.0 | 5.4 | 6.5 | 6.5 | 4.9 | 6.2 | 6.0 | 6.9 |
| | 5.3 | 6.6 | 8.0 | 6.5 | 5.8 | difficult to absorb | 6.0 | 7.8 |
| | 2.8 | 2.7 | 3.4 | 3.0 | 2.6 | | 3.1 | 3.4 |
| | 6.9 | 6.2 | 6.8 | 6.6 | 7.2 | | 7.2 | 8.8 |
| | 2.6 | 3.2 | 3.7 | 3.6 | 2.8 | | 3.6 | 3.0 |
| | 1 | 1 | 1 | | 1 | " | 1 | 1 |
| | 83.6 | 83.6 | 85.3 | 85.3 | 84.6 | 84.2 | 85.4 | 84.8 |
| | 100 | 105 | 93 | 95 | 103 | 103 | 102 | 102 |
| | 113 | 107 | n/a | 104 | 104 | 106 | 100 | 88 |

FIG. 7a-3

Modified adhesion tester used for surface application of microcapsules

LOTION in SCOTTIES SUPREME Web by Roto-Gravure Printing with "50 MIL HEX" Cylinder.

| Printed Roll Id. | Speed FPM | Lotion Residues % (w/w) | | | Handfeel Panel | |
|---|---|---|---|---|---|---|
| | | Raw Avg. | Adj. Avg. | Std.Dev'n | Average | Std.Dev'n |
| Lotion Formula AM60/PG40 | | | | | | |
| n/a | 200 | n/a | n/a | n/a | | |
| 1 | 300 | 3.58 | 3.40 | 1.11 | 100 | 9 |
| 2 | 300 | 4.62 | 4.44 | 0.05 | | |
| 1 | 500 | 4.80 | 4.63 | 0.17 | | |
| 2 | 1,000 | 2.21 | 2.04 | 0.06 | | |
| 1 | 1,000 | 3.15 | 2.98 | 0.06 | | |
| 2 B | 1,000 | 3.14 | 2.97 | 0.11 | | |
| 2A | 1,000 | 2.23 | 2.06 | 0.07 | 102 | 11 |
| 3 | 1,000 | 3.16 | 2.99 | 0.07 | | |
| 4 | 1,500 | 3.30 | 3.12 | 0.36 | 104 | 8 |
| 5 | 1,500 | | | | | |
| n/a | Nil | 0.17 | 0.00 | 0.01 | | |

FIG. 13

PHYSICAL TEST RESULTS FOR SCOTTIES SUPREME LOTIONED BY EMD's GRAVUE PRESS WITH "50 MIL HEX" CYLINDER

Product Description
CATEGORY: FACIAL
BRAND NAME: AM60/PG40 LOTION TRIALS with SCOTTIES SUPREME 3 PLY

PHYSICAL PROPERTY:

| | | Roll #1 500fpm Oct 17/00 | | | | Roll #2 1000fpm Oct 17/00 | | | | Roll #1 1000fpm Oct 18/00 | | | | Roll #2 1000fpm Oct 18/00 before trim problem and web break | | | | Roll #2 1000fpm Oct 18/00 after trim problem and web break | | | |
|---|---|---|---|---|---|---|---|---|---|---|---|---|---|---|---|---|---|---|---|---|---|
| | | Individual Plies | | | All Plies Average | Individual Plies | | | | Individual Plies | | | | | | | | | | | |
| | | B | M | T | | B | M | T | | B | M | T | | B | M | T | | B | M | T | |
| PRODUCT ATTRIBUTES | | | | | | | | | | | | | | | | | | | | | |
| BASIS WEIGHT | Lb/Rm | 10.2 | 10.2 | 10.2 | 10.2 | 10.1 | 10.7 | 10.3 | | 10.5 | 9.8 | 9.9 | | 10.1 | 9.8 | 10.1 | | 10.1 | 9.7 | 10.9 | |
| BULK-FEDERAL (24sh) | x0.001" | 44 | 50 | 48 | 47 | 48 | 46 | 48 | | 48 | 48 | 48 | | 44 | 44 | 46 | | 44 | 44 | 44 | |
| BULK-THWING (10sh) | uM | 1029 | 1077 | 950 | 1019 | 1005 | 950 | 1030 | | 1013 | 1001 | 991 | | 878 | 926 | 907 | | 897 | 931 | 923 | |
| MD STRETCH % | % | 14.0 | 14.5 | 16.8 | 15.1 | 14.4 | 14.0 | 15.5 | | 15.3 | 13.4 | 13.7 | | 15.4 | 14.0 | 14.0 | | 12.5 | 13.2 | 14.1 | |
| CD STRETCH % | % | 6.6 | 6.3 | 7.4 | 6.8 | 6.5 | 6.8 | 6.8 | | 7.4 | 6.9 | 7.0 | | 6.8 | 6.0 | 6.2 | | 6.4 | 6.8 | 6.6 | |
| MD TENSILE DRY | Oz/Inch | 12.8 | 15.8 | 18.2 | 15.6 | 14.0 | 12.8 | 15.7 | | 15.2 | 14.9 | 14.9 | | 15.1 | 15.3 | 15.3 | | 14.7 | 14.6 | 15.1 | |
| CD TENSILE DRY | Oz/Inch | 5.6 | 5.2 | 6.4 | 5.7 | 4.9 | 4.7 | 5.4 | | 5.6 | 5.1 | 4.4 | | 5.1 | 4.8 | 5.1 | | 5.3 | 4.3 | 5.6 | |

COMMENTS:
PHYSICAL PROPERTY:

| | | Parent Roll - Blank Sheet Individual Plies | | | All Plies Average | Average of Rolls at 1000 FPM Individual Plies | | | All Plies Average | Roll #4 - 1500fpm Oct 18/00 Individual Plies | | | All Plies Average | Specifications After Winder Values | |
|---|---|---|---|---|---|---|---|---|---|---|---|---|---|---|---|
| | | 1 | 2 | 3 | | B | M | T | | B | M | T | | Target | Reject |
| PRODUCT ATTRIBUTES | | | | | | | | | | | | | | | |
| BASIS WEIGHT | Lb/Rm | 9.9 | 10.0 | 10.1 | 10.0 | 10.2 | 10.0 | 10.3 | 10.2 | 9.8 | 9.9 | 10.2 | 10.0 | 9.8 | <9.2 |
| BULK-FEDERAL (24sh) | x0.001" | 48 | 50 | 50 | 49 | 46 | 46 | 47 | 46 | 44 | 44 | 46 | 45 | | |
| BULK-THWING (10sh) | uM | 998 | 1071 | 1009 | 1026 | 948 | 952 | 963 | 954 | 943 | 980 | 933 | 952 | 17.0 | |
| MD STRETCH % | % | 15.7 | 15.7 | 14.3 | 15.2 | 14.4 | 13.7 | 14.3 | 14.1 | 14.1 | 12.8 | 11.2 | 12.7 | | |
| CD STRETCH % | % | 6.7 | 6.7 | 6.7 | 6.7 | 6.8 | 6.6 | 6.7 | 6.7 | 6.6 | 6.2 | 7.0 | 6.6 | | |
| MD TENSILE DRY | Oz/Inch | 14.3 | 14.3 | 16.2 | 14.9 | 14.8 | 14.4 | 15.3 | 14.8 | 13.6 | 13.7 | 11.6 | 13.0 | 22.0 | >26.0 |
| CD TENSILE DRY | Oz/Inch | 4.7 | 4.7 | 5.2 | 4.9 | 5.2 | 4.7 | 5.1 | 5.0 | 4.5 | 5.1 | 4.1 | 4.6 | 7.5 | <3.5† |

† For Folded Sheets

FIG. 14

| Trial Variant No. | Liquid Storage & Transfer Temp C | Speed RPM | Output cc/min | Pressure Bar | Sprayer Pump RPM | Rate g/min | Time mins | Output grams | Est. Wt. Lbs. | Act. Wt. Lbs. | Air Jet PSIG | Web Speed FPM |
|---|---|---|---|---|---|---|---|---|---|---|---|---|
| | | Gear Pump | | | | | | | | | | |
| N1A | 45.0 | 5.0 | 11.7 | ? | 8.3 | 14.2 | 1.80 | 25.58 | 0.06 | 0.05 | 6.0 | 400 |
| N1B | 55.0 | ? | ? | ? | 8.3 | 12.3 | 10.25 | 125.7 | 0.28 | 0.29 | 6.0 | 414 |
| Total 1 | | | Weight of Spray in Bag = | | | 13.0 | | | 0.33 | 0.35 | | |
| N2A | 71.0 | 5.0 | 11.7 | 7.0 | 8.3 | 14.3 | 6.93 | 98.87 | 0.22 | 0.39 | 3.0 | 595 |
| N2B | | | | | 8.3 | 14.3 | 9.34 | 133.2 | 0.29 | 0.52 | 3.0 | 595 |
| Total 2 | | | Weight of Spray in Bag = | | | 25.4 | | | 0.51 | 0.91 | | |
| N3A | 71.2 | 5.0 | 11.7 | 1.5 | 8.3 | 14.3 | 9.10 | 129.8 | 0.29 | 0.39 | 3.0 | 587 |
| N3B | 70.9 | 5.0 | 11.7 | 1.4 | 8.3 | 14.3 | 9.41 | 134.2 | 0.30 | 0.30 | 2.9 | 584 |
| N3C | 70.9 | 5.0 | 11.7 | 1.4 | 8.3 | 14.3 | 9.62 | 137.1 | 0.30 | 0.31 | 2.7 | 588 |
| Total 3 | | | Weight of Spray in Bag = | | | 14.5 | | | 0.88 | 0.90 | | |
| N4A | 70.3 | 5.0 | 11.7 | 1.5 | 8.3 | 14.2 | 9.14 | 129.9 | 0.29 | 0.29 | 3.0 | 586 |
| N4B | 70.6 | 5.0 | 11.7 | 1.3 | 8.3 | 14.2 | 9.46 | 134.4 | 0.30 | 0.30 | 2.9 | 584 |
| Total 4 | | | Approximate Rate = | | | 14.5 | 9.46 | 137.2 | 0.58 | 0.59 | | |
| | | | | | | | Totals = | | 2.31 | 2.75 | | |
| N5 | 70.6 | 5.0 | 11.7 | 1.0 | 8.2 | 18.2 | 8.33 | 151.9 | 0.33 | 0.28 | 1.5 | 645 |
| N6A | 0.4 | 5.0 | 11.7 | 1.0 | 8.2 | 15.5 | 8.67 | 157.1 | 0.35 | 0.32 | 1.5 | 635 |
| N6B | 69.8 | 5.0 | 11.7 | 0.9 | 8.2 | 18.1 | 10.51 | 190.5 | 0.42 | 0.39 | 1.5 | 527 |
| Total 6 | | | Weight of Spray in Bag = | | | 16.8 | | | 0.77 | 0.71 | | |
| N7A | 69.9 | 5.0 | 11.7 | 1.0 | 8.2 | 16.0 | 10.70 | 170.9 | 0.38 | 0.37 | 1.5 | 527 |
| N7B | 70.6 | 5.0 | 11.7 | 0.9 | 8.3 | 16.2 | 13.81 | 223.3 | 0.49 | 0.48 | 1.3 | 411 |
| Total 7 | | | Weight of Spray in Bag = | | | 15.9 | | | 0.87 | 0.86 | | |
| | | | | | | | | Totals = | 1.97 | 1.85 | | |

FIG.15-1

| Carrier Liquid | | | Fragrance | | | | BATCH Total | | | Actual Use of Rolls by Weight | | | | | ADD-ON TOTAL | | | |
|---|---|---|---|---|---|---|---|---|---|---|---|---|---|---|---|---|---|---|
| Type code | Mixed Lbs | Prop w/w % | Type code | Mixed Lbs | Prop w/w % | Add-on w/w % | Density g/cc | Bulk Lbs | | Plain Net Lbs | Lotion Net Lbs | Coated Net Lbs | Coated est. Lbs | Error % | Ideal w/w % | Real w/w % | O/Spray % |
| FGWO35 | 16.33 | 100% | No | 0.00 | 0% | 0.00% | 0.863 | 16.33 | | 3.16 | 0.05 | 3.17 | 3.21 | | 1.63% | 0.32% | 80.6% |
| | | | | | | 0.00% | 0.863 | 0.00 | | 18.22 | 0.29 | 18.43 | 18.51 | | 1.61% | 1.15% | 28.5% |
| | | | | | | | Petro Can | | | 21.38 | 0.35 | 21.60 | 21.73 | 0.59% | 1.62% | 1.03% | 36.3% |
| FGWO35 | 4.77 | 95.4% | T4713 van | 0.23 | 4.60% | 0.06% | 0.87 | 5.00 | | 16.62 | 0.39 | 16.85 | 17.01 | | 2.34% | 1.38% | 40.8% |
| | | | | | | 0.06% | 0.87 est | | | 23.21 | 0.52 | 23.51 | 23.73 | | 2.25% | 1.29% | 42.7% |
| | | | | | | | | | | 39.83 | 0.91 | 40.36 | 40.74 | 0.96% | 2.29% | 1.33% | 41.9% |
| FGWO35 | 4.46 | 89.2% | T4714 C&S | 0.54 | 10.8% | 0.19% | 0.866 | 5.00 | | 22.44 | 0.29 | 22.84 | 22.73 | | 1.30% | 1.78% | -37.5% |
| | | | | | | 0.18% | 0.866 | | | 22.98 | 0.30 | 23.37 | 23.28 | | 1.31% | 1.70% | -29.6% |
| | | | | | | 0.17% | 0.866 | | | 23.64 | 0.31 | 24.01 | 23.95 | | 1.30% | 1.57% | -20.4% |
| | | | | | | | PetroLab | | | 69.06 | 0.90 | 70.22 | 69.96 | -0.38% | 1.30% | 1.68% | -29.0% |
| FGWO35 | 4.70 | 93.8% | T4715 L&F | 0.31 | 6.19% | 0.09% | 0.863 | 5.01 | | 22.60 | 0.29 | 22.93 | 22.89 | | 1.29% | 1.46% | -13.0% |
| | | | | | | 0.10% | 0.863 | | | 23.58 | 0.30 | 23.96 | 23.88 | | 1.28% | 1.61% | -25.7% |
| | | | | | | | PetroLab | | | 46.18 | 0.59 | 46.89 | 46.77 | -0.25% | 1.29% | 1.54% | -19.4% |
| Mineral Oil Based Lotions | | | | | | | | Totals = | | 176.45 | 2.75 | 179.07 | 179.20 | 0.07% | 1.56% | 1.48% | 4.7% |
| PEG200 | 2.00 | 100% | No | 0.00 | 0% | 0.00% | 1.12 | 2.00 | | 22.57 | 0.28 | 22.93 | 22.85 | -0.33% | 1.26% | 1.60% | -26.4% |
| PEG200 | 4.73 | 94.0% | T4592 L&F | 0.30 | 5.96% | 0.07% | 1.114 | 5.03 | | 23.09 | 0.32 | 23.36 | 23.41 | | 1.39% | 1.17% | 15.8% |
| | | | | | | 0.09% | PetroLab | | | 23.49 | 0.39 | 23.83 | 23.88 | | 1.66% | 1.45% | 12.6% |
| | | | | | | | | | | 46.58 | 0.71 | 47.19 | 47.29 | 0.21% | 1.52% | 1.31% | 14.0% |
| PEG200 | 2.29 | 45.5% | T4715 L&F Lipocaps | 2.74 | 54.5% | 0.12% | 0.982 | 5.03 | | 23.78 | 0.37 | 24.09 | 24.15 | | 1.57% | 1.30% | 17.2% |
| | | | | | | 0.14% | PetroLab | | | 24.01 | 0.48 | 24.39 | 24.49 | | 2.01% | 1.58% | 21.4% |
| | | | | | | | | | | 47.79 | 0.86 | 48.48 | 48.65 | 0.35% | 1.79% | 1.44% | 19.5% |
| Polyethylene Glycol Based Lotions | | | | | | | | Totals = | | 116.94 | 1.85 | 118.60 | 118.79 | 0.16% | 1.58% | 1.42% | 10.4% |

FIG. 15-2

| Trial Variant No. | Anilox Roll Ceram. Screen Lines/in | Anilox Roll Ceram. Capacity Bcm/sq.in | Plate Roll Area% | Nip Gap Web-Roll (x0.001") | Web Speed FPM | Carrier Liquid Type code | Carrier Liquid Add-On w/w % |
|---|---|---|---|---|---|---|---|
| *Trials with Frangranced Lotions on Fox 464.* | | | | | | | |
| 1 | 400 | 4 | 100 | 5 | 160 to 999 | FGWO-90 | 4.60 |
| 1A | 400 | | | | 400 | Paraflex H' | 3.25 |
| 1B | 400 | | | | 405 | Paraflex H' | 3.36 |
| 1C | 400 | | | | 725 | Paraflex H' | 2.92 |
| Average = | | | | | 510 | Paraflex H' | 3.18 |
| 2 | 400 | 4 | 100 | 5 | 999 + ?? | FGWO-90 | 3.60 |
| Actual = | | | | | 725 | FGWO-35 | 2.94 |
| 3 | 400 | 4 | 100 | 5 | 1000? | FGWO-35 | 1.60 |
| Actual = | | | | | 700 | | 0.99 |
| 4 | 400 | 4 | 100 | 5 | 160 to 999 | PEG-200 | 4.95 |
| Actual = | | | | | 650 | | 3.79 |
| 5 | 400 | 4 | 100 | 5 | 1000? | PEG-200 | 4.95 |
| Actual = | Dancer Roll Problems | | | | 700 | | 4.45 |
| 6 | 400 | 4 | 100 | 5 | 1000? | PEG-200 | 4.87 |
| Actual = | | | | | 485 | | 4.34 |
| | Dancer Roll Problem. Slowed from 700 to 425 fpm. | | | | | | |
| 7 | 400 | 4 | 100 | 5 | 1000? | PEG-200 | 4.91 |
| Actual = | | | | | 800 | | 4.14 |
| 15 | 400 | 4 | 100 | 5 | 700 | PEG-200 | 4.37 |
| Actual = | | | | | 700 | | 5.17 |
| 16 | 400 | 4 | 100 | 5 | 700 | PEG-200 | 4.25 |
| Actual = | | | | | 700 | | 5.84 |
| *Trials with Fragranced Lotions on Fox 644.* | | | | | | | |
| 17 | 700 | 2.65 | 100% o | 5 | 400 | PEG-200 | 2.00 |
| Actual = | | | | | 400 | | 2.22 |
| 18 | 700 | 2.65 | 100% o | 5 | 600 | PEG-200 | 2.00 |
| Actual = | | | | | | | 1.49 |
| 19 | 700 | 2.65 | 100% o | 5 | 600 | FGWO-35 | 2.00 |
| 19A | | | | | 600 | | 0.98 |
| 19B | | | | | 800 | | 1.20 |

FIG. 16-1

| Surfactant | | Fragrance | | Resin | | Extra Ingredients | |
|---|---|---|---|---|---|---|---|
| Type code | Add-On w/w % | Type code | Add-On w/w % | Type code | Add-On w/w % | Type code | Add-On w/w % |
| No | 0.00 | T4589 | 0.40 | No | 0.00 | No | 0.000 |
|  | 0.00 | MEC | 0.00 |  | 0.00 |  | 0.000 |
|  | 0.00 |  | 0.00 |  | 0.00 |  | 0.000 |
|  | 0.00 |  | 0.00 |  | 0.00 |  | 0.000 |
| Yes | 1.00 | T4589 | 0.40 | No | 0.00 | No | 0.000 |
| Span 85 | 0.22 | MEC | 0.42 |  | 0.00 |  | 0.000 |
| Foam in Lotion Return Line. | | | | | | | |
| Yes | 1.00 | T4589 | 0.40 | HercD | 2.00 | No | 0.000 |
| Span 85 | 0.26 | MEC | 0.49 |  | 2.49 |  | 0.000 |
| No | 0.00 | T4594 | 0.05 | No | 0.00 | No | 0.000 |
|  | 0.00 | Van.g | 0.00 |  | 0.00 |  | 0.000 |
| No | 0.00 | T4594 | 0.05 | No | 0.00 | No | 0.000 |
|  | 0.00 | Van.g | 0.06 |  | 0.00 |  | 0.000 |
| No | 0.00 | T4596 | 0.13 | No | 0.00 | No | 0.000 |
|  | 0.00 | C&S | 0.14 |  | 0.00 |  | 0.000 |
| No | 0.00 | T4592 | 0.09 | No | 0.00 | No | 0.000 |
|  | 0.00 | L&F | 0.08 |  | 0.00 |  | 0.000 |
| No | 0.00 | T4334 | 0.03 | No | 0.00 | No | 0.000 |
|  | 0.00 | Jas | 0.04 |  | 0.00 |  | 0.000 |
| No | 0.00 | T3036 | 0.15 | No | 0.00 | No | 0.000 |
|  | 0.00 | Lem | 0.21 |  | 0.00 |  | 0.000 |
| No | 0.00 | No | 0.00 | No | 0.00 | No | 0.000 |
|  | 0.00 |  | .00 |  | 0.00 |  | 0.000 |
| No | 0.00 | T4594 | 0.05 | No | 0.00 | No | 0.000 |
|  | 0.00 | Van.g | 0.04 |  | 0.00 |  | 0.000 |
| No | 0.00 | T4713 | 0.05 | No | 0.00 | No | 0.000 |
|  |  | Van.o | 0.02 |  |  |  |  |
|  |  |  | 0.03 |  |  |  |  |

FIG. 16-2

| Actual Use of Rolls as Total Net Weights | | | | | | |
|---|---|---|---|---|---|---|
| Plain Net Lbs Plain | Lotion Net Lbs Lotion | Coated Net Lbs Coated | Coated est. Lbs Coated | Add-On w/w % | Add-On Error% | Coating Loss % |
| | Press liquid system was dry at start. | | | | | |
| 236 | 7.81 | 232 | 244 | 3.31% | 4.88% | 148% |
| 196 | 6.58 | 203 | 203 | 3.35% | -0.36% | -11% |
| 228 | 6.66 | 233 | 235 | 2.92% | 0.91% | 31% |
| 660 | 21.04 | 668 | 681 | 3.19% | 1.95% | 61% |
| 218 | 7.76 | 224 | 225 | 3.58% | 0.45% | 12% |
| | | | | | Foam in | Lotion |
| 844 | 35.69 | 879 | 880 | 4.23% | 0.12% | 3% |
| 214 | 8.10 | 223 | 222 | 3.79% | -0.57% | -15% |
| 854 | 38.53 | 894 | 893 | 4.51% | -0.13% | -3% |
| 855 | 38.23 | 876 | 893 | 4.47% | 2.02% | 45% |
| 871 | 36.77 | 910 | 908 | 4.22% | -0.16% | -4% |
| 862 | 45.37 | 921 | 908 | 5.26% | -1.56% | -30% |
| 863 | 52.52 | 920 | 916 | 6.08% | -0.50% | -8% |
| Totals for Fragranced lotions printed at 4.0 BCM/sq.in. | | | | | | |
| Totals = 6,242 | 284 | 6,515 | 6,526 | 4.55% | 0.17% | 3.7% |
| 6,342 = Total includes paper used for press set-up. | | | | | | |
| 111 | 2.48 | 113 | 114 | 2.23% | 0.73% | 33% |
| 175 | 2.67 | 180 | 178 | 1.53% | -1.55% | -101% |
| 289 | 2.88 | 291 | 292 | 1.00% | 0.09% | 9% |
| 292 | 3.60 | 295 | 296 | 1.23% | 0.10% | 8% |
| Totals for Fragranced lotion printed at 2.6 BCM/sq.in. | | | | | | |
| Totals = 867 | 12 | 880 | 879 | 1.34% | -0.16% | -11.6% |

FIG. 16-3

| Lab Test Results on Bulk Lotion Liquids. | | | | |
|---|---|---|---|---|
| Viscosity testing | | Surf. Tension | Density | Residues |
| Shell cup | Brookfield | DuNouy. AS | ASTM D | Filtered |
| cP at 22C | cP at 25C | Dynes/cm | g/cc, 25C | % (w/w) |
| n/t | n/t | n/t | n/t | n/t |
| n/t | n/t | n/t | n/t | n/t |
| n/t | n/t | n/t | n/t | n/t |
| n/t | n/t | n/t | n/t | n/t |
| n/t | 80 | 30 | 0.8742 | Fibres 5.63% |
| 225 | 352 | 29 | 0.9697 | Fibers 5.67% |
| n/t | n/t | n/t | n/t | n/t |
| 50 | 76 | 38 | 1.1220 | Fibers 1.69% |
| 50 | 111 | 34 | 1.1169 | Fibers 1.99% |
| n/t | 110 | 37 | 1.1174 | Fibers 1.89% |
| 27 | n/t | n/t | n/t | n/t |
| 45 | n/t | n/t | lotion in fiber debris n/t 12.88% ex Plate Roll. 3.37% as Fiber |

FIG. 16-4

| Trial Variant No. | Anilox Roll Ceram. Screen Lines/in | Anilox Roll Ceram. Capacity Bcm/sq.in | Plate Roll Area% | Nip Gap Web-Roll (x0.001") | Web Speed FPM | Carrier Liquid Type code | Carrier Liquid Add-On w/w % |
|---|---|---|---|---|---|---|---|
| *Trials with Softner in Lotions on Fox 464.* | | | | | | | |
| 8 | 400 | 4 | 100 | 5 | 160 to 999 | PEG-200 | 3.00 |
| Actual = | | | | | 525 | | 3.11 |
| Fibre Build-Up on Plate Roll. Slowed from 800 to 525 fpr Foam in Lotion Return Line. | | | | | | | |
| 9 | 400 | 4 | 100 | 5 | 1000? | PEG-200 | 0.90 |
| Actual = | | | | | 400 | FGWO-35 | 1.15 |
| Fibre Build-up slings off at 1000 layers if standing. | | | | | | | |
| 10 | 400 | 4 | 100? | 5 | 1000? | PEG-200 | 0.90 |
| Actual = NOT RUN | | | 0 | | 0 | | 0.00 |
| 11 | 400 | 4 | 100 | 5 | 1000? | FGWO-35 | 0.90 |
| Actual = | | | | | 400 | | 1.40 |
| Fibre Build-Up. Ran 400 to 5000 fpm. | | | | | | | |
| *Trials with Softner in Lotions on Fox 644.* | | | | | | | |
| 20 | 700 | 2.65 | 100%o | 5 | 400 | FGWO-35 | 0.55 |
| 20A | | | | | 400 | | 0.96 |
| 20B | | | | | | | |
| *Trials with Fragranced Microcapsules in Lotions on Fox 464.* | | | | | | | |
| 12 | 400 | 4 | 100 | 5 | 1000? | FGWO-90 | 0.50 |
| Actual = | | | Fibre Build-Up. | | 500 | | 1.49 |
| 13 | 400 | 4 | 100 | 5 | 1000? | PEG-200 | 0.50 |
| Actual = | | | Fibre Build-Up. | | 500 | | 2.38 |
| 14 | 400 | 4 | 100 | 5 | 1000? | No | 0.00 |
| Actual = | | | Plate Roll Clean & Hot after. | | 900 | PEG-200 | 4.79 |
| 21 | 250 | 6 | 100%o | 5 | 700 | FGWO-35 | 4.45 |
| Actual = | | | | | 583 | | 5.19 |
| 22 | 250 | 6 | 100%o | 5 | 700 | PEG-200 | 4.29 |
| Actual = | | | | | 300 | | 7.32 |

FIG. 17-1

| Surfactant | | Fragrance | | Resin | | Extra Ingredients | |
|---|---|---|---|---|---|---|---|
| Type code | Add-On w/w % | Type code | Add-On w/w % | Type code | Add-On w/w % | Type code | Add-On w/w % |
| 8600 | 2.00 | No | 0.00 | No | 0.00 | No | 0.000 |
|  | 1.35 |  | 0.00 |  | 0.00 |  | 0.000 |
| Fibre Build-Up on Plate Roll. Slowed from 800 to 525 fpr Foam in Lotion Return Line. | | | | | | | |
| 8600 | 1.30 | No | 0.00 | No | 0.00 | No | 0.000 |
|  | 1.00 |  | 0.00 |  | 0.00 |  | 0.000 |
| 8600 | 1.30 | No | 0.00 | No | 0.00 | Aloe, VitE | 0.011 |
|  | 0.00 |  | 0.00 |  | 0.00 |  | 0.000 |
| 8600 | 1.30 | No | 0.00 | No | 0.00 | Aloe, VitE | 0.011 |
|  | 2.03 |  | 0.00 |  | 0.00 |  | 0.040 |
| 8600 | 1.40 | T4713 | 0.05 | No | 0.00 | No | 0.000 |
|  | 1.43 | Van. o | 0.03 |  | 0.00 |  | 0.000 |
| 8600 | 1.30 | 9850C | 0.40 | No | 0.00 | Aloe, VitE | 0.011 |
|  | 0.96 | Baby | 0.39 |  | 0.00 |  | 0.000 |
| 8600 | 1.30 | 9850 C | 0.40 | No | 0.00 | Aloe, VitE | 0.011 |
|  | 0.81 |  | 0.51 |  | 0.00 |  | 0.000 |
| 8600 | 1.80 | 9850C | 0.40 | No | 0.00 | Aloe, VitE | 0.011 |
|  | 0.00 |  | 0.76 |  | 0.00 |  | 0.000 |
| No | 0.00 | No | 0.00 | No | 0.00 | 3M Microcaps | 0.150 |
|  | 0.00 |  | 0.00 |  | 0.00 | Red Shell w | 0.078 |
|  |  |  |  |  |  | Yellow Shell w | 0.087 |
| No | 0.00 | Lipocap | 0.10 | No | 0.00 | 3M Microcaps | 0.011 |
|  | 0.00 | MEC. o | 0.20 |  | 0.00 | Red Shell w | 0.105 |
|  |  | water | 1.00 |  |  |  |  |

FIG. 17-2

| Actual Use of Rolls as Total Net Weight | | | | | | |
|---|---|---|---|---|---|---|
| Plain Net Lbs | Lotion Net Lbs | Coated Net Lbs | Coated est. Lbs | Add-On w/w % | Add-On Error% | Coating Loss % |
| 471 | 21.47 | 466 | 492 | 4.56% | 5.65% | 124% |
| Leaks in pan. Fibres coating plate roll & flakes off above 500 fpm. | | | | | | |
| 625 | 13.39 | 638 | 638 | 2.14% | 0.08% | 4% |
| 0 | 0.00 | 0 | N/A | N/A | N/A | N/A |
| 867 | 30.11 | 891 | 897 | 3.47% | 0.59% | 17% |
| Totals for Softner lotions printed at 4.0 BCM/sq.in. | | | | | | |
| Totals = 1,962 | 65 | 1,995 | 2,027 | 3.31% | 1.64% | 49.6% |
| 278 | 6.91 | 286 | 285 | 2.49% | -0.55% | -22% |
| 244 | 5.86 | 249 | 250 | 2.40% | 0.13% | 6% |
| Totals for Softner lotions printed at 2.6 BCM/sq.in. | | | | | | |
| Totals = 521 | 13 | 535 | 534 | 2.45% | -0.23% | -9.5% |
| 283 | 8.04 | 289 | 291 | 2.84% | 0.75% | 26% |
| 328 | 12.11 | 333 | 340 | 3.69% | 2.19% | 59% |
| 290 | 15.06 | 304 | 305 | 5.20% | 0.42% | 8% |
| Totals for microcapsules printed at 4 BCM/sq.in. | | | | | | |
| Totals = 900 | 35 | 925 | 935 | 3.91% | 1.17% | 29.9% |
| 174 | 9.30 | 179 | 183 | 5.36% | 2.52% | 47% |
| 102 | 8.83 | 108 | 111 | 8.65% | 3.31% | 38% |
| Totals for microcapsules printed at 6 BCM/sq.in. | | | | | | |
| Totals = 276 | 18 | 286 | 294 | 6.58% | 2.81% | 42.8% |

FIG. 17-3

| Lab Test Results on Bulk Lotion Liquids. | | | | |
|---|---|---|---|---|
| Viscosity testing | | Surf. Tension | Density | Residues |
| Shell cup | Brookfield | DuNouy, AS | ASTM D | Filtered |
| cP at 22C | cP at 25C | Dynes/cm | g/cc, 25C | % (w/w) |
| 125 | 350 | 23 | 1.0451 | Fibers 3.59% |
| 270 344 | 266 | 24 | 0.8784 | Fibers 6.45% |
| n/t | n/t | n/t | n/t | n/t |
| >1,200 | 1,108 | 26 | 0.9115 | Fibers 2.96% |
| | | | | 4.33% as Fiber |

Microcapsules dropping out in mix bucket
| >>1,200 | 480 | n/t | n/t | n/t |

Increased viscosity (& ucaps) in pail after trial.
| >>1,200 | 632 | n/t | n/t | n/t |
| | 5,032 | n/t | n/t | n/t |

Increased viscosity (& ucaps) in pail after trial.
| 80 | 142 | n/t | n/t | n/t |
| | 2,440 | n/t | n/t | n/t |

Increased viscosity (& ucaps) in pail after trial.

FIG. 17-4

RESULTS FROM FLEXOGRAPHIC COATING OF SCOTTIES 2 PLY CREPED PAPER

| | | fox #16 | fox #15 | fox #5 | fox #7 | BASELINE Plain, Folded | fox #11 Coated | vin #26 Coated "Slab" Samples | vin #27 | vin #28 | vin #29 | BASELINE Plain, Slab |
|---|---|---|---|---|---|---|---|---|---|---|---|---|
| Softner DC8600 | % w/w | 0.00 | 0.00 | 0.00 | 0.00 | 0.00 | 2.03 | 5.40 | 7.00 | 12.60 | 1.30 | 0.00 |
| Mineral Oil, Aloe, Vit.E | % w/w | 0.21 | 0.04 | 0.06 | 0.08 | 0.00 | 1.44 | 0.00 | 0.10 | 8.38 | 0.87 | 0.00 |
| Polyethylene Glycols | % w/w | 5.84 | 5.17 | 4.45 | 4.14 | 0.00 | 0.00 | 0.00 | 0.00 | 0.00 | 0.00 | 0.00 |
| TOTAL LIQUID ADD-ON | % w/w | 6.08 | 5.26 | 4.51 | 4.22 | 0.00 | 3.47 | 8.88 | 11.69 | 20.98 | 6.17 | 0.00 |
| TRIAL VARIANT CODE | | Coated and Folded Sheets | | | | | | | | | | |
| PRODUCT ATTRIBUTES | | | | | | | | | | | | |
| BASIS WEIGHT | Lb/Rm | 20.0 | 20.1 | 20.0 | 20.0 | 18.1 | 20.1 | 19.6 | 20.2 | 25.6 | 18.6 | 19.4 |
| BULK-Federal tester (24 sheets) | x0.001" | 146 | 144 | 140 | 143 | 147 | 149 | 152 | 140 | 148 | 144 | 154 |
| BULK-Thwing Albert tester (1 sheet) | microns | 1971 | 1931 | 1899 | 1982 | | 2151 | | | | | |
| MD STRETCH | % | 9.5 | 10.6 | 9.7 | 10.4 | 13.7 | 9.8 | | | | | |
| CD STRETCH | % | 4.9 | 4.7 | 5.2 | 5.2 | | 4.3 | | | | | |
| MD TENSILE DRY | Oz/Inch | 11.4 | 12.4 | 12.1 | 13.0 | 16.6 | 10.8 | 12.2 | 11.8 | 11.2 | 10.6 | 17.2 |
| CD TENSILE DRY | Oz/Inch | 4.1 | 3.7 | 4.1 | 4.6 | 5.2 | 3.4 | 4.0 | 4.6 | 4.6 | 4.55.2 | 6.1 |
| MD WET TENSILE (nat) | Oz/Inch | 5.9 | 4.8 | 6.1 | 6.2 | | 6.5 | 4.7 | 4.4 | 7.9 | | 6.0 |
| CD WET TENSILE (nat) | Oz/Inch | 2.6 | 2.5 | 2.8 | 2.8 | | 2.5 | | | | | |
| MD WET TENSILE (art) | Oz/Inch | 6.5 | 5.7 | 6.4 | 7.2 | 8.1 | 5.3 | 4.5 | 43 | 6.7 | 4.4 | 6.3 |
| CD WET TENSILE (art) | Oz/Inch | 2.8 | 3.4 | 3.5 | 2.7 | | 2.7 | | | | | |
| ABSB. 1-PLY SEC./.01cc | Sec. | 0.1 | 0.1 | 0.1 | 0.1 | 0.1 | 1.8 | 61 | 25 | 180 | 21 | 0.1 |
| BRIGHTNESS - GE @ 452 nm | % Refl. | 88.3 | 88.3 | 88.2 | 88.3 | | 87.6 | 86.1 | 84 | 82.4 | 87.3 | 87.7 |
| CLEANLINESS FACTOR | | | | | | | | | | | | |
| SOFTNESS (HANDFEEL) | VWS | 85 | 85 | 87 | 88 | 84 | 94 | 94 NW-B.309 | 96 NW-B.311 | 95 NW-B.309 | 98 NW-B.311 | 78 NW Panels |
| CHROMATICITY COORDINATES | L* | 97.1 | 97.0 | 97.0 | | | | | | | | |
| | a* | -0.58 | -0.57 | -0.53 | | | | | | | | |
| | b* | 3.19 | 3.16 | 3.21 | | | | | | | | |
| COLOUR VALUES | ASTM WH | 74.7 | 74.8 | 74.5 | | | | | | | | |
| | ATSM YEL | 4.83 | 4.79 | 4.86 | | | | | | | | |
| | CIE WH | 78.13 | 78.16 | 77.93 | | | | | | | | |
| | CIE TINT | -0.91 | -0.91 | -1.01 | | | | | | | | |

FIG. 18

TISSUE PRODUCTS CONTAINING SOFTNESS

CROSS-REFERENCE TO RELATED APPLICATIONS

The present application is a continuation of U.S. application Ser. No. 10/297,053, now U.S. Pat. No. 7,597,780, filed May 21, 2003 under 37 U.S.C. 371, based on International Application No. PCT/CA02/00475, filed Apr. 8, 2002, which in turn claims the priority benefit of U.S. Provisional Patent Application No. 60/282,143, filed Apr. 9, 2001, the disclosures of which are hereby incorporated by reference in their entireties.

FIELD OF INVENTION

This invention relates generally to tissue paper, and more specifically to tissue paper having a soft tactile feel, a process for the production of tissue paper having softeners and particular compositions of said tissues.

BACKGROUND TO THE INVENTION

Tissues are widely used for a variety of uses including nose care, removal of cosmetics, eye glass cleaning and wipe ups around the home. Such tissues have gained widespread use for a variety of reasons including the relative inexpensiveness of the product and thus disposability of the tissues.

Such tissue papers require a variety of characteristics depending on their usage. For example softness is a major benefit when the tissue papers are used for nose care or removal of cosmetics. Tissues used for wipe ups, however, generally require absorbency while non-smearing is a preferred benefit when using tissue papers for eyeglass cleaning. Generally speaking most individuals prefer strength of the product for most applications.

Softness of tissues can be imparted to the substrate paper by a variety of means including mechanical and chemical processes. The resiliency, flexibility or smoothness of the tissue may perceive softness of the product.

Mechanical softness may be imparted to the paper by a variety of means including calendarizing which affects the loft or the bulkiness of the paper.

Chemical softness may be imparted to a tissue paper by means of adding or imparting chemical compounds.

For example U.S. Pat. No. 4,950,545 describes facial tissues containing a silicone compound which is incorporated into the tissue with an aqueous carrier having a smear index of 1.0 or less, a lint reduction index of 5 or greater, and sink time no more than 30 second greater than sink time of the same facial tissue without the silicon compound.

Moreover U.S. Pat. No. 5,059,282 teaches a tissue paper comprising cellulostic fibres and an effective amount of polysiloxane material, said polysiloxane being uniformly disposed on the outwardly facing surfaces of the tissue paper, said effective amount of polysiloxane being from about 0.004% to about 2% polysiloxane based on the dry fibre weight of said tissue paper, said polysiloxane having a viscosity of about 25 centistokes or more, said tissue paper after aging two weeks after its manufacture has a wetting time of two minutes or less.

Moreover U.S. Pat. No. 5,552,020 discloses tissue products made by adding one or more softeners/debonders and a silicon glycol copolymer of the paper making fibres at the wet end of the tissue machine, prior to the formation of the tissue web. Suitable softeners/debonders disclosed include organo-reactive polysiloxanes, quaternary ammonium compounds, quaternized protein compounds, phospholipids and silicon quaternaries. One such binder material is starch.

U.S. Pat. No. 5,059,282 also discloses the use of surfactants. Specific surfactants used in tissue paper are disclosed in an article entitled "The Roll of Silicones in Non-Woven Fabric Applications" by A. J. Sabia and R. P. Metzler in Non-Wovens Industry, September 1983, pp. 16 to 22 namely on page 20, "Surfactants selected for polymer emulsification can also have an important effect on performance of the organo-reactive silicones."

The use of a 2% amino-silicone injected into a pulp slurry has been taught in U.S. Pat. No. 5,908,707 where a conventional tissue tissue/towel paper substrate is formed, dried and creped in a conventional manner in the formation of wet-like cleaning wipes.

DISCLOSURE OF INVENTION

It is an object of this invention to provide tissues having improved softness characteristics.

It is another object of this invention to provide creped paper tissues having improved softness characteristics for facial, hand and related personal uses.

It is a further object of this invention to provide a optimum combination of features to the substrate tissue in the softness and feel of the product by applying a composition to the tissue with low dosage costs. It is a further object of this invention to provide an improved method of producing same.

BRIEF DESCRIPTION OF DRAWINGS

FIG. 4 is a chart for mixtures prepared for lotionizing trials.

FIG. 5 is a chart including viscosity and surface tension of the formulas by item codes.

FIGS. 7a and 7b are charts showing softness of Scotties Supreme versus various lotions and doses.

FIG. 13 is a table showing test results for Lotion Formula AM60/PPG40 applied by rotogravure printing with a 50 millinch hexagonal pattern cylinder at various RPM's and the handfeel results.

FIG. 14 shows the physical test results for the bottom middle and top ply web referred to in FIG. 13.

FIGS. 15 and 16 show test results utilizing mineral oil based lotions and polyethylene glycol based lotions with fragrance.

FIG. 17 shows test results utilizing a carrier with DC 8600 and fragrance.

FIG. 18 is a table showing results of FIG. 17.

BEST MODE FOR CARRYING OUT THE INVENTION

Figure 1A:
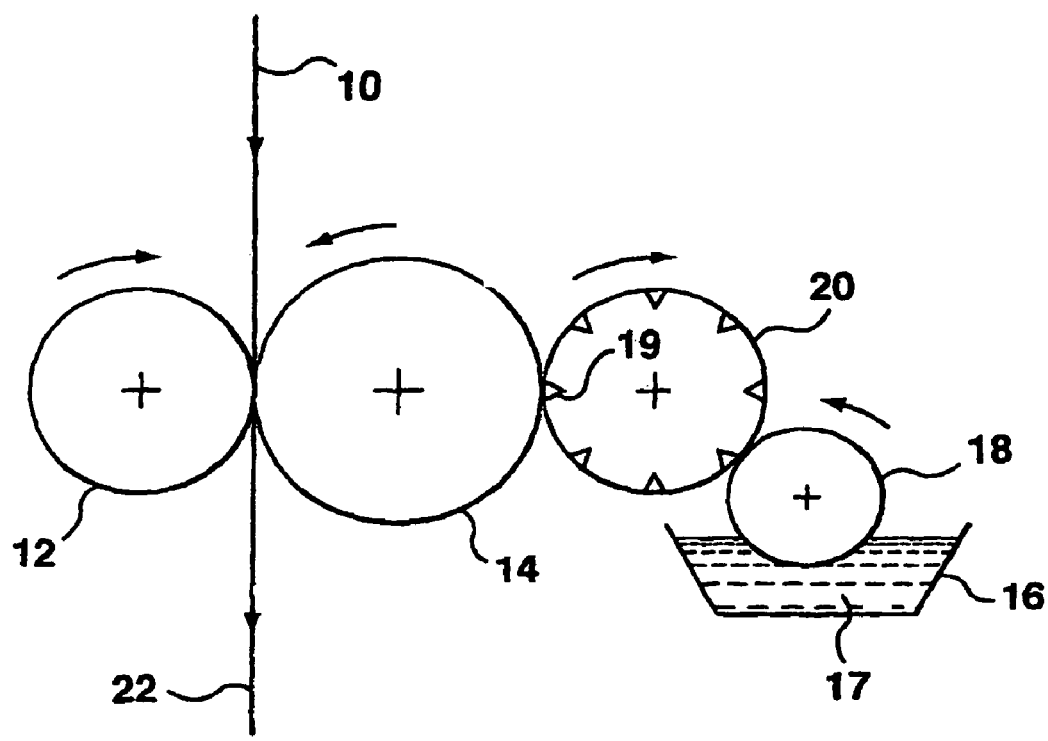
FIGS. 1(a) and (b) generally illustrate a flexographic press and flexographic closed cavity fountain system respectively.

In the description that follows, like parts are marked throughout the specification and the drawings with the same respective reference numerals. The drawings are not necessarily to scale and in some instances proportions may have been exaggerated in order to more clearly depict certain features of the invention.

Overview of the Invention

Generally speaking a compound has been applied to tissue paper to impart improved softness characteristics. Amino silicone polymer is a major contributor to any gain in softness. Excellent qualities were realized with a Super Mix as defined herein. The composition or lotion is applied to the substrate by spraying or pressing unto the cellulostic fibers.

EXAMPLES OF PROCESSES FOR APPLYING THE LOTION

The preferred method of lotionizing a web of paper includes flexographic printing press, spraying and rotogravure printing.

Figure 1B:
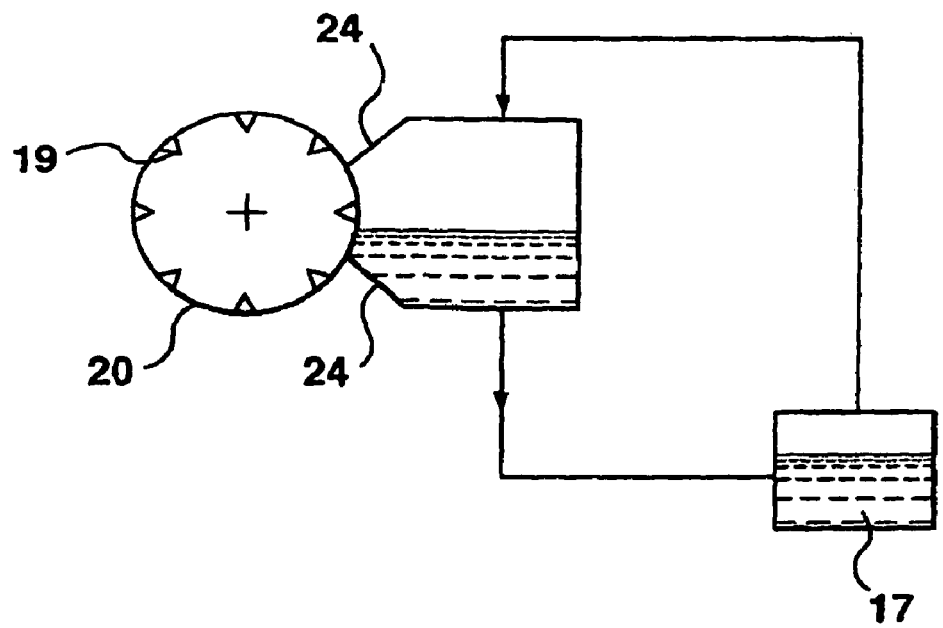

More specifically FIGS. 1(a) and 1(b) generally describes the process of applying the composition or lotion to a substrate by a flexographic press. Generally speaking the method of applying a lotionizing composition onto a web or substrate of cellulostic paper comprises feeding a plain web of tissue paper 10 between a backing roll 12 and plate roll 14 which rotate for example as shown in FIG. 1(a). The fountain or ink pan 16 contains the lotion 17 described herein which are picked up by the pick up roll 18 and then transferred to the anilox roll or cylinder 20. The anilox roll 20 is engraved and/or etched 19 as is well known to persons skilled in the art so as to transfer the composition of lotion to the plate roll 14 to coat the web 22.

Although FIG. 1(a) shows the application of the lotionizing composition to one side of the web 10, this invention should not be so limited as both sides of the web may be coated.

Furthermore FIG. 1(b) shows a variation to the flexographic press of 1(b) showing a closed cavity fountain system as is well known to persons skilled in the art illustrating doctor blades 24 to scrape excess lotion 17.

The flexographic press illustrated can include heating systems, edge embossing and folder features well known to these persons skilled in the art.

For example a flexographic press with an "all over" coating roller may apply lotion. Such roller may have a 360 screen rating and a 5.6 micron cell depth where two rubber surface rollers transfer liquids from the inkwell to an anilox roller and from the anilox roller unto the moving web. Such example has been given for illustrative purposes only and should not be construed as limiting the invention.

Figure 2:
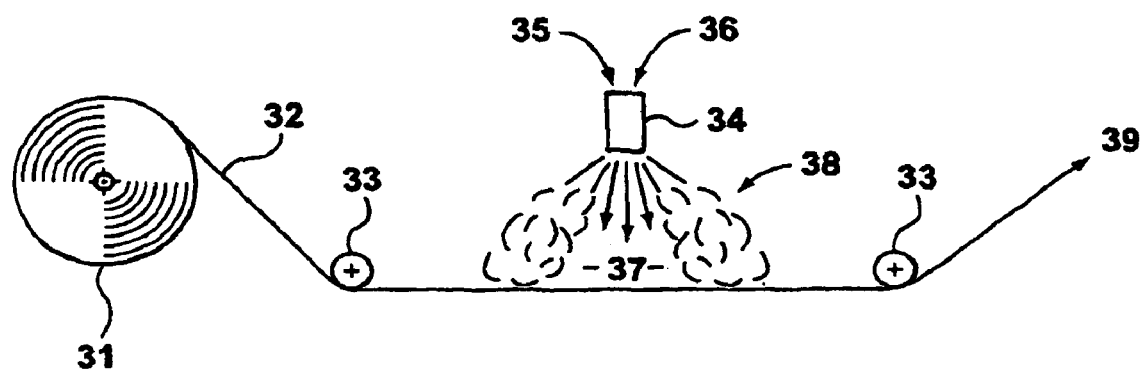
FIG. 2 generally illustrates a sprayer for coating the moving web of paper.

FIG. 2 illustrates the application of lotion or composition unto a moving web by means of spraying nozzles. It is preferable to spray lotion with an electrostatic charge for delivering accuracy and minimal overspraying. More specifically FIG. 2 illustrates a parent roll 31 which has wound creped paper tissue which is plain or uncoated.

The numeral 32 represents at least one ply of plain creped tissue paper which is unwound and moving under tension towards the sprayer. The idler roll 33 helps to is keep tension on the web 32 and can distribute tensile force across the web (such as for example the use of a "Mount Hope" roll).

The spray nozzle or nozzle 34 mixes together liquids or lotions 35 and air 36 before spraying. The spray nozzle 34 can be adjusted to vary the outflow of direct flow of aerated lotion 37 by changing the orifice size and the like in a manner well known to those persons skilled in the art.

The top-down orientation is not strictly necessary for spraying paper webs but helps to minimize losses by aerosol mists of lotion 38 and over spray. Supply of lotion 35 is generally kept under constant pressure, by a pump, and may be filtered and/or heated as required. The flow rate can be adjusted. The supply of air 36 such as a compressed air supply is generally kept at fairly constant pressure and filtered, dried or dry and at room temperature before spray mixing. Coated web of paper 39 leaving spraying zone is drawn to the next operation (e.g. drier unit, ply bonder, folder or rewinder).

Figure 3:
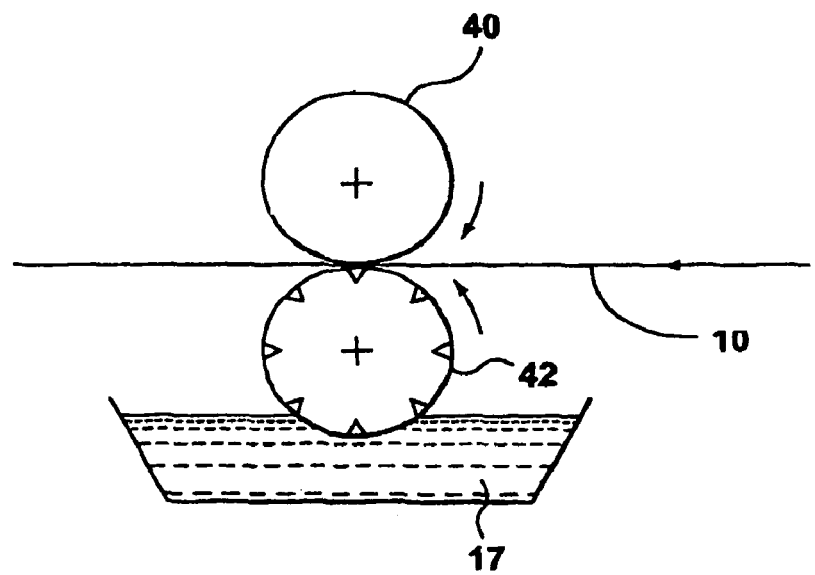
FIG. 3 illustrates a roto gravure press.

FIG. 3 illustrates schematically a roto gravure press having a backing roll 40 such as a rubber impression roll, a gravure roll 42 such as an engraved roll contacting the lotion 17, where the underside of the web 10 is treated with lotion 17. In one example the rotogravure press may comprise a "50 Mil Hex" pattern engraved into the cylinder's face to approximately 50 microns depth with cell capacity approximately 3.9 billion cubic microns per square inch of pattern surface area.

Paper Substrate

The trial paper substrate utilized in many of the comparative studies to be described herein was comprised of Scotties Supreme 3 ply paper, however, the invention should not be limited to such tissue paper since the advantages of the invention may be realized by utilizing two ply or one ply paper or other suitable cellulostic fibers.

For example Scotties Supreme 3 ply paper can comprise of:
55% by wt of bleached eucalyptus pulp (E)
45% by wt of bleached northern softwood kraft (BNSK) such as Domtar Q90 cellulostic fiber substrate. The BNSK can include pine, some spruce or perhaps cedar fibers. Depending on the type of substrate one experiences variations in tactile qualities.

The term cellulostic generally refers to the tissue being cellulose but generally can include other chemicals, such as binding agents to help "glue" or "cement" the various fibers together used during typical paper making operations.

One substrate that can be utilized includes:
35% wt E
45% wt recycled fibers
20% wt BNSK.

The compositions or lotions disclosed herein improve the tactile or softness qualities of the substrates described. Generally speaking, however, such tactile or softness characteristic are more pronounced when utilizing 55% by wt E as compared to 35% by wt E.

Compositions Used During Trial Run

FIG. 4 is a chart which illustrates the various chemicals that were utilized in the trial runs for applying to the tissue paper which were then subjected to a variety of tests relating to softness, bulk, stretch and tensile strength.

More specifically the item code Am relates to an amino silicone composition which has been applied to a moving web of Scotties Supreme tissue. More specifically the item code Am relates to a diamino-functional silicone polymer which is supplied by Dow Corning under their item DC 2-8040. Typically properties of the Dow Corning DC 2-8040 of the diamino-functional silicone polymer relates to a viscosity of 800-5000 centipoise and a non-volatile content of 95%. The invention however should not be limited to the specific supplier item referred to herein but rather is an example of the amino silicone that may be used.

Likewise the item code Sur referred to in FIG. 4 relates to the compound Dimethicone Copolyol supplied by Dow Corning under the supplier item DC-190 which typical properties include a viscosity of 1500 c.p. at 25 degrees C. Dow Corning's 190 surfactant acts as a surface tension depressant, and wetting agent.

The compound Dimethicone Copolyol may originate from other sources. Furthermore as can be seen from FIG. 4 the item Sur has been blended with the amino silicone namely Am in the ratio of 25% by weight of Sur and 75% by weight of Am. Both compounds have been blended as indicated by the column entitled "Direction Action" and the formula has been designated in the column entitled "Formula by Item Codes" as Am 75/Sur 25.

The column Soh relates to silanol functional fluids which are polydimethyl siloxane polymers with terminal silanol reactivity. One example of the silanol functional fluids originates from Dow Corning and identified by the supplier item DC Q1-3563 as can be seen from FIG. 4 where 25% by weight of Soh has been blended with 75% by weight of Am and designated by the formula Am75/Soh25.

The column Sil refers to a "coupling agent" available from Dow Corning under the trade designation DC Z-6040 Silane. This material is reported to be a coupling agent for chemicals and is thought as potentially useful to improve the lotioned paper as needed. Such improvements may include bond formation or adhesion between any of the chemicals or substrates applied unto to the paper web and the paper fibers that are mainly cellulose.

FIG. 4 also illustrates the Item Code Mo, which relates to a highly refined white mineral oil originating from Petro Canada and designated by the supplier item Purity WO15. By way of example five compositions of Mo were tested, namely:

90% by weight of Mo and 10% by weight of Sur
60% by weight of Mo and 40% by weight Sur
25% by weight of Mo and 75% by weight Am
75% by weight of Mo and 25% by weight Am
100% by weight of Mo.

The column entitled 802 Witco PA-802 relates to a blend of nonionic and cationic surfactants. In one embodiment these surfactants originate from Goldschmidt (formerly Witco) under the designation Arosurf PA-802.

Furthermore waxes were also tested as shown in FIG. 4 and are identified by the Item Code W. One such example of waxes that have been used originates from the supplier IGI Waxes under the supplier item Micro 5702.

Moreover propyl-glycol was also tested and shown in FIG. 4 as Item Code Pg originated from Ashland.

Finally polypropoxylated-stearyl alcohol was also tested and designated by the Item Code PPG supplied by Goldschmidt under their supplier number PPG-11 Stearyl Ether.

The Item Code PPG was utilized in two test runs namely a Super Mix which is hereby being used as a short form for the following approximate composition by weight percent, namely:

| | |
|---|---|
| 18.8% | amino silicone |
| 18.8% | dimethicone copolyol |
| 18.8% | silanol functional fluid |
| 18.8% | white mineral oil |
| remainder = 100.0% | polypropoxylated stearyl alcohol. |

Moreover PPG was also used in the formula by Item Code Am60/PPG40. Note Am60/PPG40 is identical to AM60/PG40, as used herein.

FIG. 5 summarizes the trial runs of the lotionizing formula by Item Codes as shown including the viscosity and surface tension of same as particularized therein.

Objectives of the Lotionizing Trials

An 18 inch wide web of Scotties Supreme was lotionized by utilizing the composition formulas referred to above. More specifically such formulations were applied to the web of celluostic fiber by:
  flexographic press with a folder
  flexographic press with dryer and folder
  spray nozzle with dryer and folder.

Once the lotion was applied to the web, samples were prepared into sheets of folded facial tissue. Generally speaking such samples were prepared at two to three doses for each lotion. Thereafter the samples were tested to discover the effects of the lotion on the paper by formulation and dosage so as optimize:
  (a) the relationship between hand feel (softness) and dose;
  (b) dose on absorbency, bulk and tensile strength.

Figure 6:
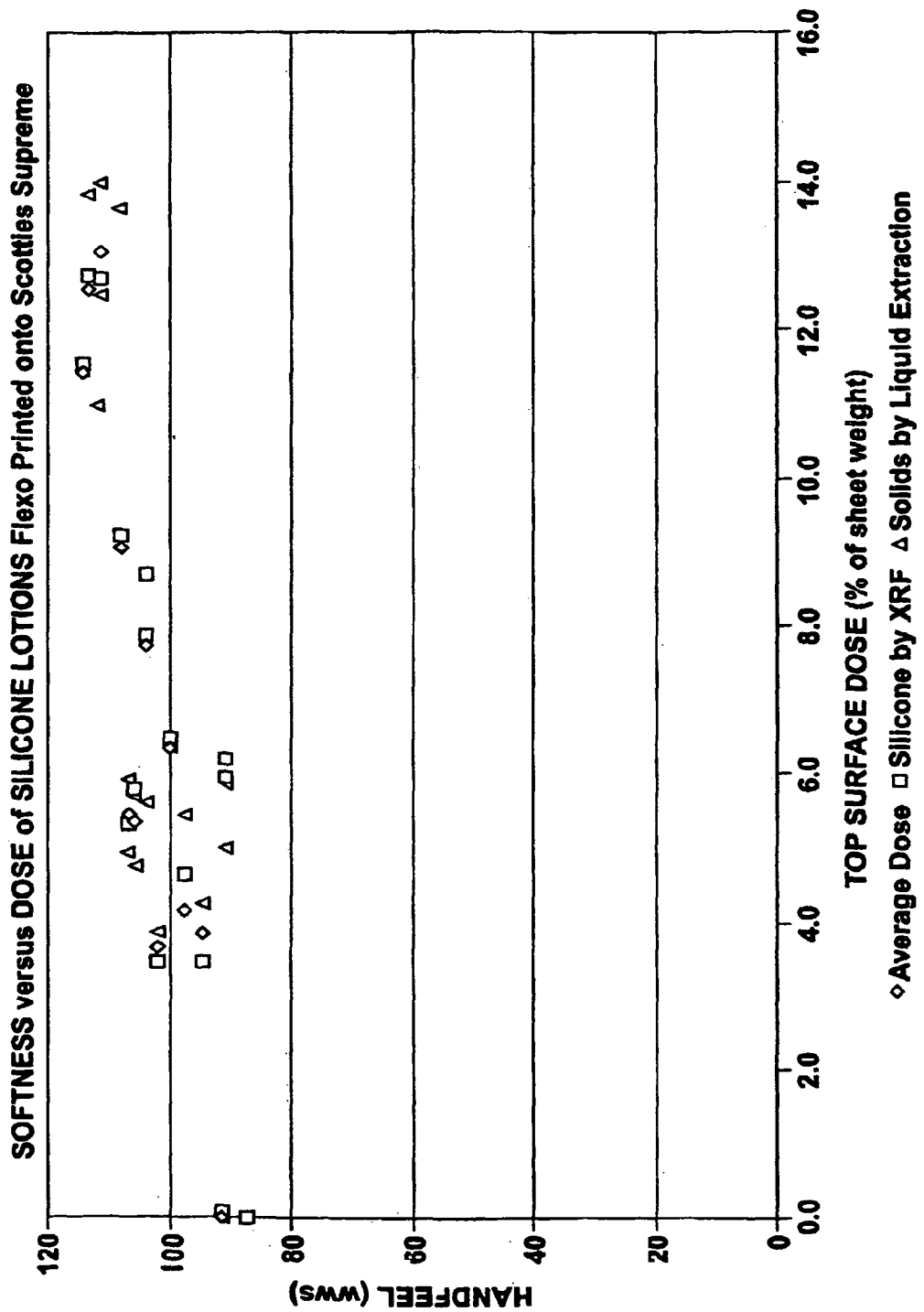
FIG. 6 is a softness versus dose of silicon lotions chart which have been flexo printed unto Scotties Supreme.

FIG. 6 is a chart of the softness verses dose of silicon lotion flexoprinted unto Scotties Supreme substrate.

In particular the web of tissue was lotionized in a flexo press:
  (a) at speeds of 300-600 feet per minute;
  (b) where up to 13% of lotion was added on by weight of the sheet of tissue at high viscosity;
  (c) a viscosity range of 10 to 4,500 centipoise was tested;
  (d) with surface tensions of 21 to 70 dynes/centimeter;
  (e) two separate doses were practical for each lotion.

Furthermore a dryer was utilized to help distribute lotions and overcome coarse flexomat. A high temperature is generally better than ambient temperature and a dryer temperature was tried between 100 to 165 Celsius.

Furthermore interfolded tissues were prepared at web speeds of up to 600 feet per minute.

Specific Parameters for Gravure Press to Lotionized Facial Tissue

A 70 inch web of regular three ply Scotties Supreme ex HMD PM 5 was utilized in the gravure press described above at various speeds from 300 to 2000 feet per minute. Such web was lotionized with the ingredients referred to above and in particular the formula Am60/PPG40.

The lotion was transferred by a gravure cylinder unto the bottom ply of the web. The lotion add on was approximately 3% to 4% of sheet weight and somewhat decreased with speed. Printing speeds tested were approximately 300, 500, 1000 and 1500 feet per minutes. Print impression roll load can be varied from nil to 225 pounds per inch of width along the entire nip where paper web passes between the impression roll and gravure cylinder.

Such lotionized paper was then wound unto paper rolls with Am60/PPG40 at speeds to 1500 feet per minute.

FIG. 6 illustrates that there were a number of formulations, which exhibited a hand feel greater than 105 WWS, which was tested in accordance with a method to be disclosed herein. A hand feel of 105 WWS was chosen as a minimum desired goal as this represented the maximum current hand feel which is attainable by prior art means.

FIG. 6 is a more detailed histograph of the softness of Scotties Supreme with various lotions as identified above plus those components referred to below and doses as it relates to hand feel. In particular FIG. 7 shows that the formula Am60/PPG40 demonstrated hand feel values of 112 and 110 WWS while the Super Mix had values of 113 and 107 respectively. It should be appreciated that such softness values relate to a 3 ply tissue paper, and that different values would be observed if 2 ply or 1 ply tissue were to be utilized. Generally speaking the hand feel of a 2 ply tissue paper coated with Am60/PPG40 would exhibit a value of approximately 95 WWS while a one ply would be lower.

Figure 7B:
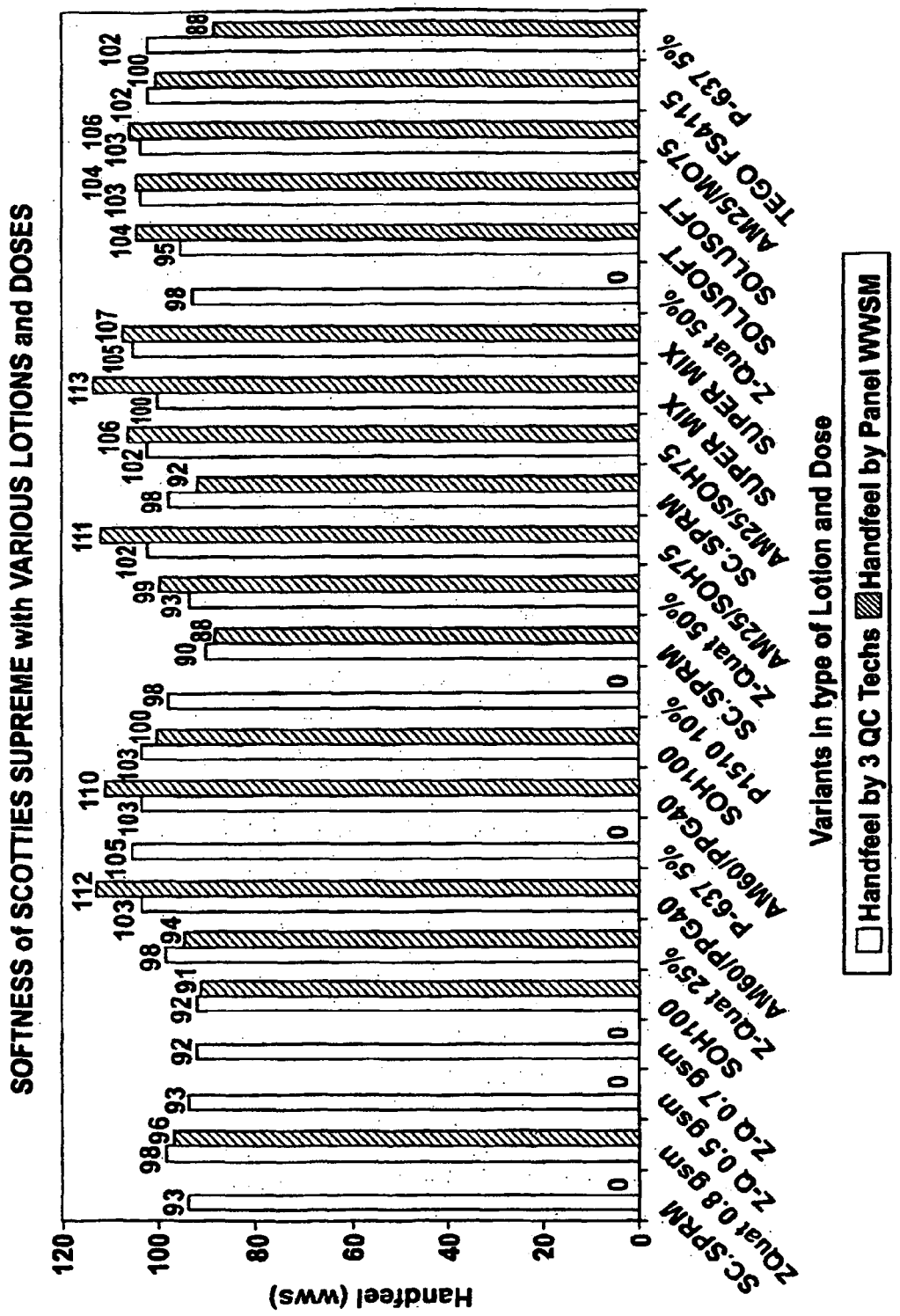

More specifically FIG. 7a is a chart showing the testing of 23 lotioned variants of 3 ply Scotties Supreme (trade mark) against reference of plain Scotties Supreme identified by column 100. FIG. 7b represents the data in FIG. 7a in a histograph form.

For example when 101 in FIG. 7a represents the variant 101 in FIG. 7b identified as Z Quat 0.8 gsm. Z Quat is a trade name for a modified aliphatic amine available from Goldschmidt Chemical Corp. under product identification EXP-5398-4. More specifically 0.8 gsm (i.e. 0.8 grams per meter of tissue) are applied and subjected to the tests referred to in FIGS. 7a and 7b. Likewise variant 103 relates to 0.7 gsm of Z Quat applied to the Scotties Supreme tissue, and tested as referred to herein.

Variant 104 relates to the silanol functional fluids referred to earlier. Variant 105 relates to applied 25% by weight of Z Quat and 75% by weight of Ethanol 96% (i.e. EtOH), with a calculated dose of lotion on the web of 4 Kg/MT.

Variant 107 relates to 5% of P-637 which is a proprietary commercial mixture available from ChemPro Inc., mixed with 95% water and applied to the Scotties Supreme web at 7 Kg/MT.

Variant 108 relates to the formulation AM60/PPG40 referred to earlier applied to the web at a measured dose of 91 average Kg/MT and calculated dose of 40 Kg/MT.

Variant 110 relates to 10% of P1510 which is Arosurf PA-802 (described herein), mixed with 90% water by weight.

Variant 111 and 114 relate again to the reference Scotties Supreme.

Variant 119 and 120 relate to a substrate under the trade name Solusoft WA which is a proprietary commercial mixture of principally silicone polymers at 30 to 35% by weight of an aqueous mixture as supplied by Clariant AG where variant 119 so is applied in a flexo gravure fashion while variant 120 is sprayed unto the web.

Figure 8:
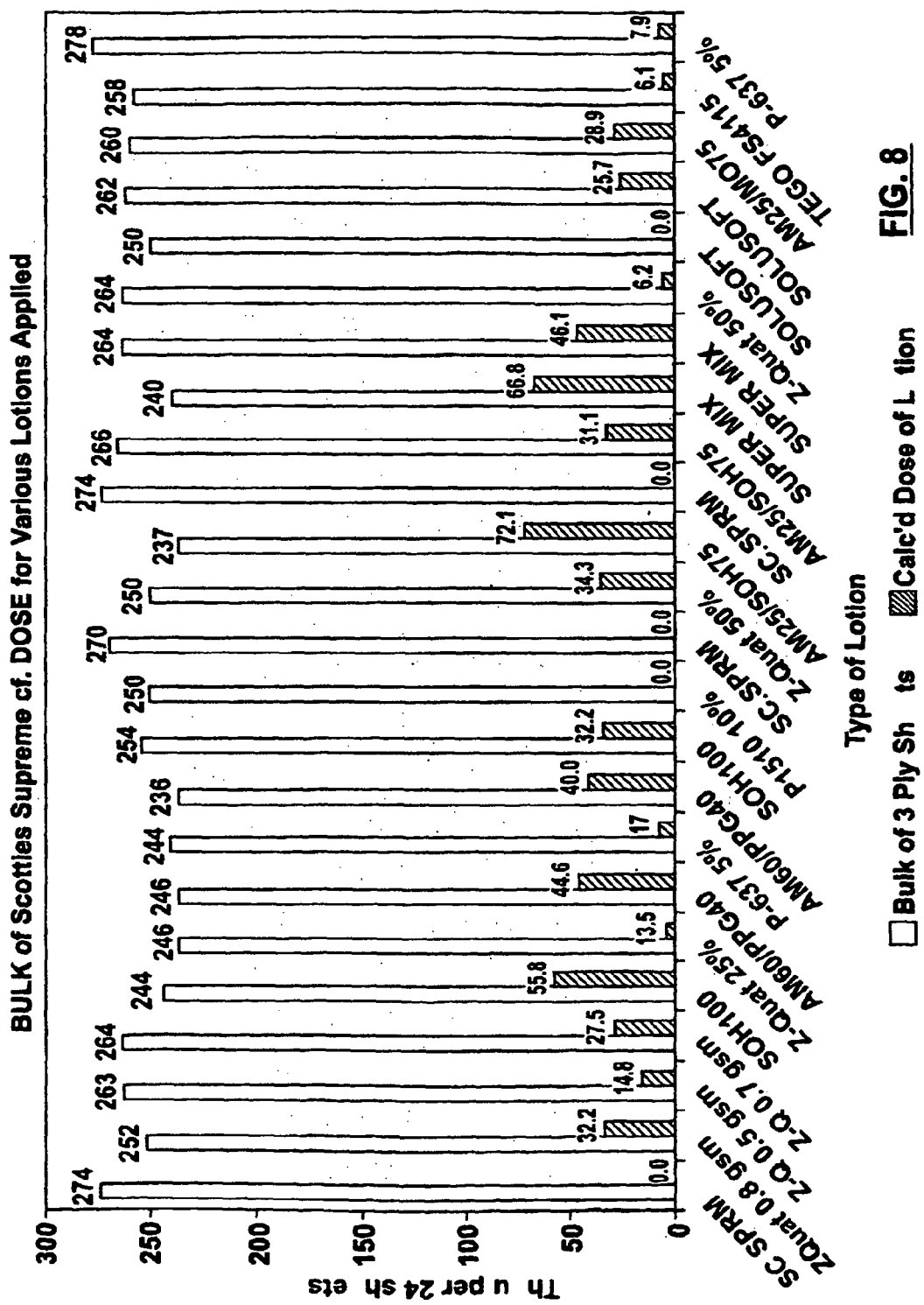
FIG. 8 is a chart entitled bulk of Scotties Supreme with dose of various lotions applied.

Finally variant 122 relates to applying a substrate under the trade name Tego FS41 which is available from Goldschmidt Chemical which is a proprietary commercial blend of organopolysiloxane of approximately 32% non-volatile materials. FIG. 8 is a histograph of the bulk of Scotties Supreme with the calculated dose of various lotions applied as tested in the manner to be described herein.

Figure 9:
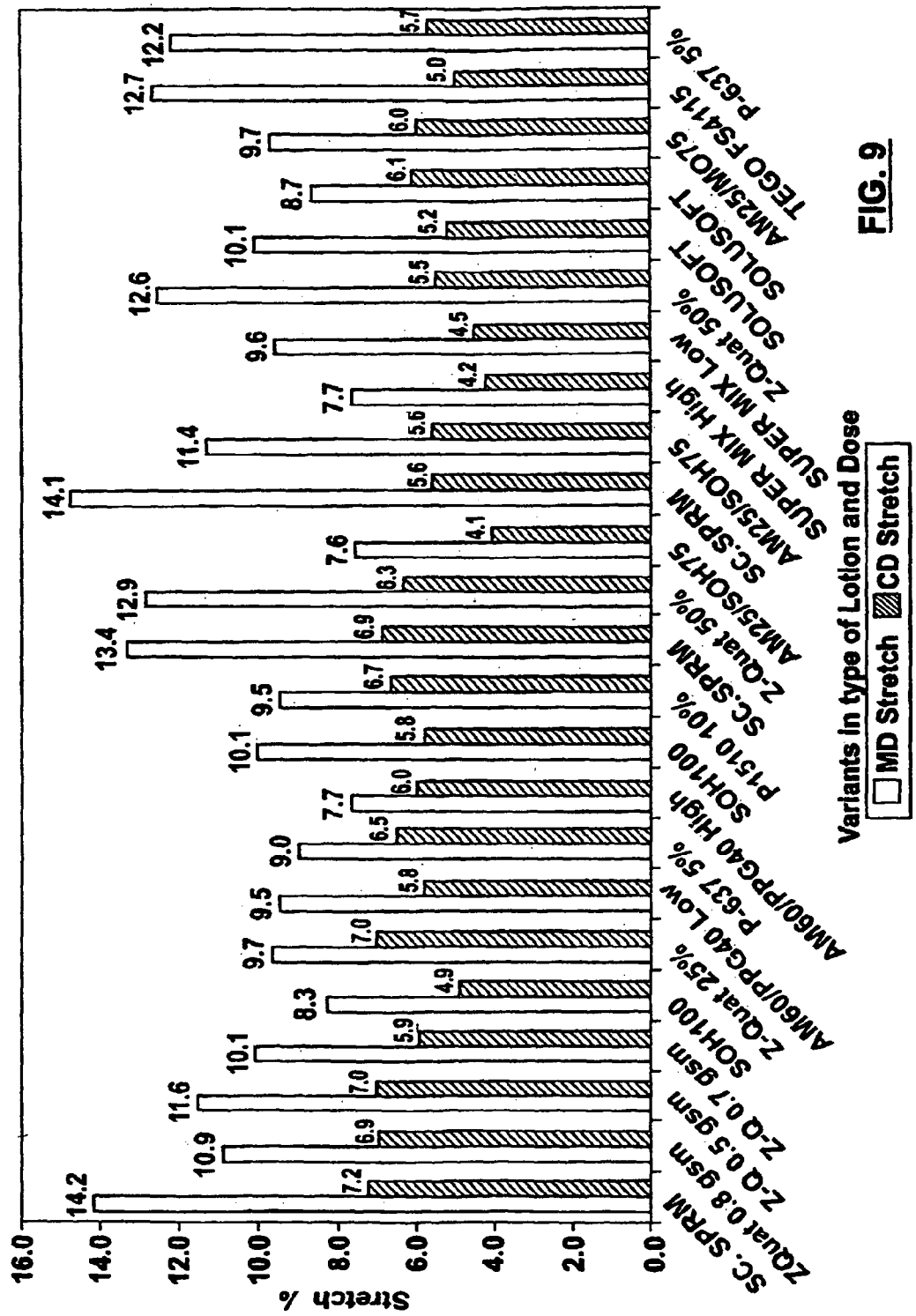
FIG. 9 is a chart entitled stretch of Scotties Supreme with various lotions and doses.

Moreover FIG. 9 is a histograph of the stretch of Scotties Supreme with various lotions and doses where MD relates to stretch in the machine direction while CD relates to stretch in the cross machine direction.

Figure 10:
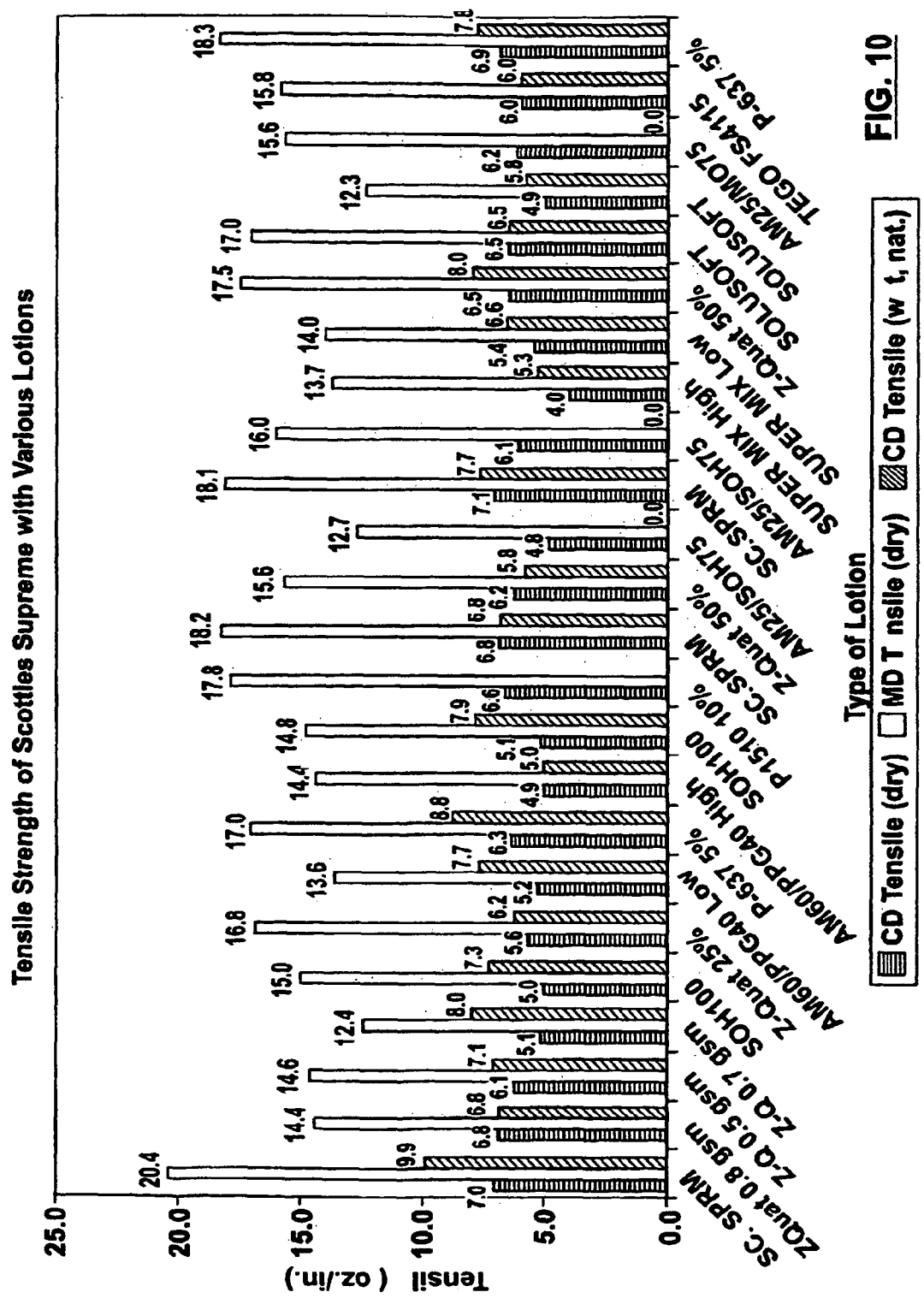
FIG. 10 is a chart entitled tensile strength of Scotties Supreme with various lotions.
Figure 11:
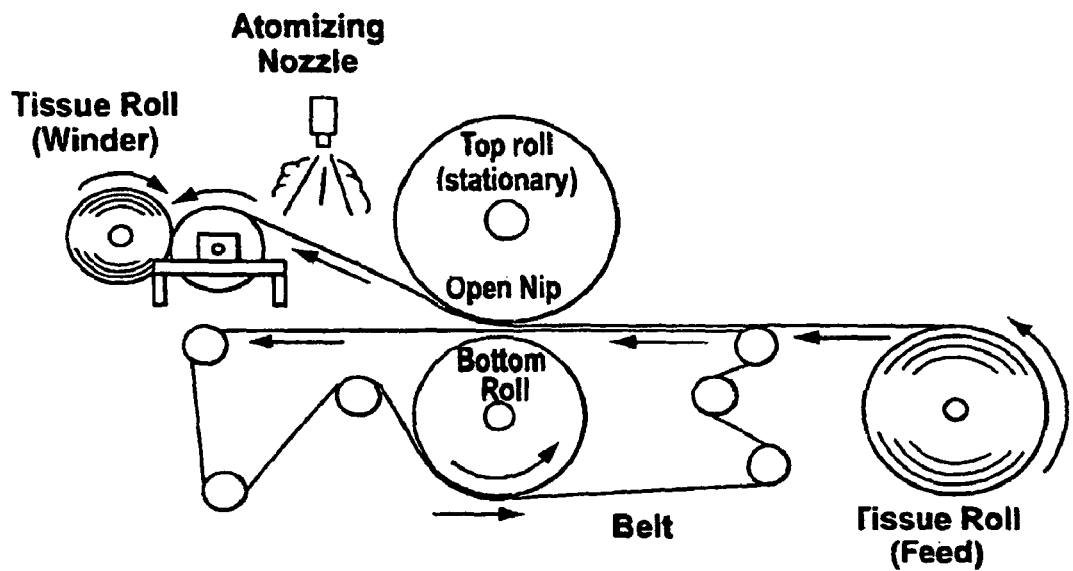
FIG. 11 is an illustration of the apparatus used for application of microcapsules to tissue paper.

Moreover FIG. 10 relates to the tensile strength of Scotties Supreme with various lotions as illustrated. There are a number of methods that can be used to estimate the doses of lotion added to the substrate. Such methods include:
(a) for flexopress—the weight of the whole web sample is taken before the dryer;
(b) spray—the ratio of the weight of lotion delivered by nozzle that lands on the web in 60 seconds to the weight of the web area passing beneath in the same period of time;
(c) the weight of folded sheets taken after the dryer;
(d) weight of materials extracted by solvents from folded sheets taken after the dryer;
(e) weight of silicone polymer determined in sheets by X-ray analysis.

In each method, a gain in weight was calculated by determining the difference in weight between lotionized paper and the plain untreated paper substrate used at a time closest to the time of actual treatment.

In some cases, as for example, in methods 1 and 2 referred to above, when the weight of treated paper was less than the closest blank resulted in a negative difference, (i.e. loss rather than gain) the target rate for the bare sheet would be used.

The estimates of dose or "add-on" are then calculated and expressed in percentage terms as the algebraic ratio of the gain in weight from the lotion added to the original weight of the plain paper as used.

Results

An analysis of the materials referred to above shows that amino silicone polymer is a major contributor to any gain in softness. A review of the figures show that the highest doses of lotion with increased compositions of amino silicone gave generally the best hand feel values. However lotions with high content of amino silicone were viscous and difficult to manage requiring high levels of dilutant (e.g. hydroxy-silicone) to decrease the viscosity of the mixture and surfactant (e.g. polyoxygenated oils) to allow water penetration to the treated paper.

It was found that amino silicone coating on paper is hydrophobic unless blended properly with suitable hydrophilic materials. Regardless, amino-silicones adhere well to paper fibers.

Moreover anhydrous lotions containing amino silicone were best for increased tissue paper softness. Water based lotions required the dryer to quickly remove excess moisture from the web before the paper disintegrates. Thus increased water content in a lotion limits the effective dose.

However non-aqueous liquids did not require a heating zone to remove water but benefited from heat energy to improve distribution of lotion ingredients through the matrix of cellulose fibers in the paper web. Furthermore, exposure to radiant heating better maintained the original post-treatment absorbency for lotionized AM60/PG40 and Super Mix samples over the 7 months of aging since preparation.

Many lotions in the past tended to decrease the tensile strength of the paper substrate. Generally speaking lotionized papers with a high improvement in softness also have low tensile strength and/or large losses in original tensile strength.

However it was unexpectedly observed that the Super Mix and compositions having amino silicones had high perception of softness and relatively good balance of tensile strength. Also unanticipated was the reduction in tissue dust or "lint" for Super Mix and AM60/PG40 lotionized paper tissued.

Moreover as can be seen from the figures paper bulk was depreciated minimally by lotionizing, but there was some indication that some of the lotions added to the loft.

Furthermore it was observed that migration of the lotion to adjacent plies occurred in the roll between printing and conversion. Initially the improved softness was felt on the treated surface of the 3 ply web. After lotionized rolls aged two weeks, it was more difficult to know which ply has been originally treated. Lotion ingredients migrated between the treated ply and adjacent plies while the rolls were stored or were in transit. This improved the sheets overall tactile.

Therefore the results of the tests referred to above showed:
(a) amino silicone was a contributor to softness;
(b) blends were needed for spray nozzles and printing presses;
(c) the dilution chemicals used to reduce the viscosity of the amino silicone also depreciated the expected gain in tensile strength from the amino-silicone;

(d) the hydroxy silicone did not really add to the paper softness but served well as a satisfactory extender or dilutant of the amino silicone;

(e) several lotioned paper samples were made which met facial tissue standard of 105 WWS;

(f) non-water based lotions were found to be best for increasing tactile softness.

Perception of Softness (note by "appeared" we mean perceived by touch not sight) The figures shown herein illustrate good softness for: Am60/PPG40

Super Mix

The Super Mix appeared relatively "wetter" while the Am60/PPG40 appeared relatively "drier" than the other by hand feel.

Hand Feel Panel Test

The hand feel test is based on a "paired-comparison" technique while the panelist assess samples "blind" without seeing them. Each sample is compared to every other sample, including reference standards, by every panelist. The preferred sample is rated on a scale from 1 to 9. Results are immediately recorded by the panel facilitator before proceeding to the next comparison. Ratings range from 1 to 9 where one is equal and nine is totally different. Three known standard samples must be used along with typically four unknown samples. Standards are intended to span the range of interest. Typically, ten panelists are included. Therefore, a typical handfeel panel generates 210 separate preference comparisons. The data points are then analyzed by a "least squares" linear regression algorithm. Statistical values of average and standard deviation are calculated for all handfeel standards and interpolated for each unknown sample for each panelist and the overall result. Similarly, panel quality control statistics are calculated for determining the accuracy (i.e. correlation coefficient r) and inconsistency (inconsistency coefficient i) for each panelist and the entire group. Results from one or more panelists and the group can be disqualified based on poor quality control data as compared against historical values. In the case of disqualifying some panelist(s), those values are excluded and the remaining panelists' data is reanalyzed. Handfeel panel data are considered satisfactory when derived from eight or more qualified participants.

By utilizing the hand feel test described one can generate world wide scott values (WWS) and determine the perceived softness when tested against a baseline sample.

Alternatively softness may be determined when more than 50% of people recognize an improved hand feel when comparing the coated paper with uncoated paper substrate.

Hand Feel Test for Quality Control

The following steps were undertaken to determine hand softness, namely:

(a) fold a specific number of sheets into a sample pad by folding in half once, then fold in half again. The sample is four sheets thick.

(b) ensure crepe side is in—smooth side (drier side) on the outside of the pad;

(c) roll products—ensure when folding that the outside of the roll is on the outside of the pad;

(d) select a standard which is closest to the target for the product one is testing;

(e) take a standard pad in one hand and test pad in the other. Compare the two for cushion, flexibility and surface feel, (f) cushion—does the test sample feel thick or flat compared to the standard sample (g) flexibility—does the test sample feel flexible, crushable or is it stiff compared to the standard (h) surface feel—does the test sample feel smooth or harsh compared to the standard sample (i) if the test sample is softer, select the next highest standard available. If the test sample is less soft select the next lowest standard.

(j) compare the test sample verses the new selected standard (k) continue this way until one has "bracketed" the test sample into two standards (l) if the test sample is equal to a standard, record the standard feel as the hand feel rating of the test sample (m) if the test sample is between the two standards, record the average of the two standard value (n) ratings are recorded in increments of five. Enter the rating into the system.

Alternatively improved softness may be determined where more than 50% of people recognize an improved handfeel when comparing the coated paper with uncoated paper substrate.

Determining Tensiles and Stretch

The following test was conducted to determine tensiles and stretch 1. cut an 8 inch section from the sample submitted by the machine room;
2. strips are cut in both machine direction MD and cross direction CD;
3. place the sample in a strip cutter so that the strip is cut parallel with the direction being cut;
4. clamp MD or CD set of strips in upper jaw of tensile tester, ensuring strips are straight;
5. place the specified number of plies in the lower jaw, clamp in place. Strips should be drawn tight enough to eliminate slack without pulling out any crepes.
6. Activate the test button. Stretch reading is displayed as elongation EL. Tensile strength is labelled L.
7. Test five samples and average. Enter the average stretch and tensile into the system.

Determine Wet Tensile

The following procedure was conducted to determine the wet tensile, namely:

1. cut tensile strips
2. place strips in hot plate at 300 degrees F. for two minutes
3. fold the strips in half and dip into a beaker of distilled water at room temperature. One end of sample length should be saturated at the center. Ensure the sample is wet through all plies.
4. Clamp sample in upper jaw of tensile tester.
5. Place specified number of plies in lower jaw, clamp in place. Strips should be drawn tight enough to eliminate slack without pulling out any crepe.
6. Activate the test button. Tensile is labelled L.
7. Test five samples and average. Enter the average wet tensile into the system.

Determining Basis Weight

The following procedure was utilized to determine basis weight, namely:

1. a 13 inch section is cut from the sample submitted by the machine room.
2. The section is cut using the electronic cutter and the appropriate die.
3. A sample of the reel 8 plies thick is cut out using the 8 sheet die.
4. A sample of the rewinder 12 plies thick is cut out using the 12 sheet die.
5. The reel checks of the paper machine, the sample is weighed after cutting and the weight recorded into the system.

6. Samples from the rewinders are conditioned before weighing namely:

five minutes for grades with the basis weight under 15 pounds 8 minutes for grades with the basis weight of 15 pounds or higher.

7. After conditioning the sample is weighed and the results entered into the system.

Determining Bulk

The following procedure is utilized to determine bulk:

1. bulk is tested using the same sample what was used for determining basis weight.
2. Measure bulk by placing sample between plates of bulker.
3. Slowly release the plunger, applying the pressure gradually.
4. When the plunger is fully compressed, take readings to the nearest one thousandths of an inch. Take three readings and average.
5. Reel checks from the paper machines are measured for bulk after cutting them out.
6. A sample of the reel paper machine and samples of rewinders are conditioned before measuring bulk as referred to above. Enter the average bulk into the system.

Hydrophilic Softener

Good results have also been experienced by utilizing a hydrophilic softener such as DC8600 available from Dow Corning. Furthermore the DC8600 to be described herein can be used for toilet tissue, towels, serviettes and the like.

DC 8600 hydrophilic softener is classified as hydrophilic amino copolyol as particularized in U.S. Pat. No. 6,136,215. The "backbone" polydimethylsiloxane (i.e. PDMS) is well known to be hydrophobic, but is not a greasy feeling. PDMS improves the flexibility or drape character when applied to non-woven webs with a significant content of paper fibers, thereby PDMS improves the overall tactile sensation. PDMS alone, however, causes deterioration of the fibrous web by loss of tensile strength.

Accordingly PDMS was modified by various functional groups or "side chains" along its length. Numerous polyoxygenated chains (e.g. polyethylene-polypropylene glycol allyl methyl ether) found in DC 8600 impart hydrophilicity to the molecule permitting it to be miscible with water, but this does not depreciate the handfeel. Side groups of hydrocarbon fatty alcohol radicals found in DC 8600 with varying carbon chain lengths improve the handfeel by offering a more luxurious tactile sensation, which is not greasy feeling, as these too are bound to the PDMS. Numerous amino and amide functional groups attached whether directly or indirectly to PDMS offer enhanced bonding sites with the relatively more electronegative functional groups found on adjacent surfaces (e.g. hydroxyl functional groups of the cellulose paper fibers) and/or with water molecules present in the air at typical ambient conditions of temperature and relative humidity. So called "hydrogen bonding" from water molecules can form "bridges" to occur virtually everywhere along the modified PDMS molecule between adjacent attractive groups and contribute to the spatial stability of the polymers and close fibers by intramolecular and intermolecular means. Furthermore, the amino functional groups are well known to enhance the tensile strength of the predominantly cellulose fiber matrix when so treated and, consequently, this improves the so called "wet-strength" of the web after being wetted by water or another liquid which may contain some water (e.g. ethanol).

DC 8600 lacks a significant content of water. Additional drying, therefore, is not an absolute requirement for topical application onto a dry web containing fibers of paper, etc. Experience has shown, however, that further exposure to a source of heat after such topical application removes traces of water and tends to improve dispersion of the added constituents throughout the matrix of the fibrous web and increase and/or speed up bonding adherence and/or association between any of the polymers and/or other constituents and the individual fibers of the web and/or cross-links or associations between several fibers of the web and/or cross-links or associations with any content of the 8600 to itself within the fiber matrix of the web and/or at the exterior of the web (e.g. a surface coating).

The DC 8600 hydrophilic softener can be applied topically onto the external surfaces of a moving web of non-woven fibrous material in single or multiple plies by a printing press or spray nozzle as described above. However, the DC 8600 can also be added into a water based batch of pulps and other paper making chemicals. Preferably the 8600 is added directly to the batch of pulp fibers in water before any other chemicals are added. Furthermore, agitation or mechanical mixing (e.g. in a pulper and/or refiner) with or without extra heating, will enhance the natural dispersion of the hydrophilic polymer throughout the batch and close association with, including surrounding and/or adherence to, the wet paper fibers while at the "wet-end" of a paper-machine.

The treated pulp mixture will then be processed as is typical in paper making. For example, the treated pulp mixture is released via a headbox "slot" or "jet" onto a moving wire belt (e.g. "Fourdrinier" or in addition to a Fourdrinier wire, initial de-watering can be done by a "twin wire former" where the sheet is initially de-watered as a function of fabric, tensions and roll radius) for water removal by gravity drainage then suction drainage by vacuum boxes and mechanical expression by pressing felts and by a pressure nip formed between adjacent rollers and/or vacuum suction rollers. Residual water in the semi-dry fibrous web is typically evaporated while it contacts or passes over a heated surface or heated air passing through the web, or heating means. By way of example such heat surface may be a drum dryer (i.e. Yankee), through air dryer, or the like. Additional chemicals, with varying quantities for surface coverage, are typically sprayed onto the drum dryer surface and/or the web. This is, firstly, to help adhere to bind the semi-dry web onto the contact surface of the drum dryer and, secondly, to help release the dried web during creping. One or more scraping blades are typically used to remove or "peel-off" the dry web from the dryer surface and to mechanically soften or "crepe" the paper on the rotating drum by collision of the paper with the stationary blade edge. Finally the dry web is wound into large rolls or "reels" at a moisture content of 15% or less by weight of the dry web, ideally at 10% or less moisture, and most preferably at about 4% moisture or less.

Calendaring of the dry web may or may not be completed after the treated web is dry. Calendaring is done to increase the surface smoothness or gloss of the paper. Calendaring can also be done on the just dried tissue paper web immediately after exiting the creping blade adjacent the "Yankee" drying section but before the reeling section of the paper machine, where the flat web is wound to form of reel. Typically, calendaring is done soon after reels have been made and during simultaneous unwinding of one or more reels. The paper web passes between the pinch-point or "nip" of a vertical stack of horizontal calendar rolls or cylinders and is rubbed on the exposed surfaces by contact with the rotation of the adjacent rolls' hardened polished metal (e.g. iron) surfaces). The various webs of one ply will be immediately layered, with or without physical adhesion or chemical adhesives, to form a continuous sheet with multiple plies that is then wound into a new reel or "Parent Roll".

Such a treated web of dry non-woven fibers may or may not be completely used for forming a multiple ply sheet. It is possible to use only reels of treated single ply web for the exterior plies of a multiply sheet and untreated reel(s) for any inner ply(s) or any other combination for reasons of economy, handfeel or softness for tactile appreciation, tensile strength whether expressed as dry or wet tensile strength, cushion or bulkiness, and/or another desired paper attribute.

Typically good results were experienced by applying from 0.05% to 25% by weight of DC 8600 to a non-woven web of predominantly air-dry paper fibers by weight. Preferably, the topical applied dose ranges from 0.1% to 15% by weight. Whereas, the dose when applied by pulping is preferably 0.1% to 3.0% by weight of the dry air fibers. The paper fibers to be used are, preferably, predominantly of cellulose but could include a fraction of up to 50% by weight as lignin-cellulose and/or rayon and/or synthetic filaments.

Example of Process Description (for Coating Fibers with DC8600 in i.e. "Wet End" of a Paper Machine)

The following is an example of a process description to prepare a web of light dry creped (LDC) tissue paper whose fibers are coated with DC8600 in the "wet end" of a paper machine.

The furnish is composed of bleached softwood kraft pulp, such as Canfor HS400 pulp in a proportion of 44%, and bleached acacia pulp in a proportion of 56%. The pulp is received as dry lap and reslushed at a consistency of about 5% (solids) in a so-called pulper with "white water" recirculated from the paper machine. Once uniformly repulped, the pulp is pumped to a "dump chest" and then to a "machine chest". Then, from the machine chest the pulp is pumped through a "refiner".

A refiner is generally equipment made of two grooved discs—one rotating and one immobile where pulp is fed between such discs through the immobile disc. The purpose of the refiner is to develop strength by increasing the specific surface of fibers through the delamination and fibrillation. The refiner was operated at approximately 200 Mega Watts per Tonne of pulp finish.

After the refiner, the pulp continues to a "regulator", which generally consists of a constant level regulation box. The pulp is fed to the middle chamber of the regulator and baffles are used to level the access of the pulp to the accept side and the reject side. The reject side goes to a stock return tank which is then pumped to the machine chest. The accept side is fed to the bottom of the "wire pit" into a chamber leading to the inlet of a "fan pump". In this manner, "white water" from the wire pit is mixed with the pulp at the inlet of the fan pump. The blend is then fed to a pressure screen to remove any contaminants. The accept side of the pressure screen goes to the "headbox". The reject side goes to a vibrating screen such as for example a Finckh screen, where the rejects are sewered and the accept goes back to the wire pit.

The headbox distributes the pulp suspension evenly across the paper machine width. The headbox throws the pulp suspension on a wire that lets part of the water (eventually called "white water") go through to the wire pit and that retains fibers on its surface, forming the web. The wire is endless, and rotates around cylinders. The drainage area is an inclined "Fourdrinier" type. At the end of that area, the sheet is transferred to a felt with the help of a "pick up shoe". A pick up shoe is a device that uses vacuum on the other side of the felt to transfer the sheet from the wire surface unto the felt surface.

Then another felt bottom belt joins the top felt with the sheet in the middle. This goes through a first pressing stage, where pressure is applied by means of two rolls pressing against each other. The water in the sheet is expressed to the felts and the sheet reduces its water content. After that pressing stage, the sheet remains on the top felt and continues to the second pressing stage, where the sheet is now pressed between a pressure roll (applying the pressure) and a Yankee dryer. The Yankee dryer is approximately a 12 foot diameter rotating cylinder, containing steam, used to dry the paper. Prior to the application of the sheet onto the Yankee dryer, some coating is sprayed on the Yankee dryer surface. This coating is composed of Hercules' Crepetrol 8115 (120 cc/min) and Release Agent 8312 (12 cc/min) and is sprayed on the surface of the Yankee with a water carrier. The Yankee has a tangential speed of 3100 feet per minute. The spray of Release Agent 8312 was reduced after the add-on of 5 kg of DC8600 per Tonne of air dry pulp fibers, commensurate with increasing content of the softeners in the web, and eventually "shut-off" between 5 and 10 kg of DC8600 per Tonne (i.e. 1000 kg).

The rotational speed of the reel was increased with increasing softener content on the fibrous web above approximately 5 kg of DC8600 per Tonne.

At 10 kg DC8600 per Tonne with creping adhesive Crepetrol 8115 as used, however, the web did not adhere very well to the Yankee surface causing ineffective creping. Symptoms included "loose sheet" as seen on the Yankee, poorly wound reels, a coarse crepe pattern on samples of the LDC paper and lab handfeel measurements had deteriorated.

After that second pressing stage, the sheet remains on the surface of the Yankee and undergoes the final drying step. The Yankee dryer is covered by a gas-fire hood, which contributes to dry the paper faster. Once dried and containing 3-4% moisture, the sheet is peeled off the Yankee surface by means of a "creping blade". This blade is as long as the Yankee dryer is wide and is applied against the surface of the Yankee.

The sheet then goes through a calandering stage, where the sheet passes between two steel rolls and pressure is applied. The speed of the sheet at that point is approximately 2630 feet per minute. The surface of the sheet is made flatter and softer by this process step. Then the sheet is wound into reels and finally, two reels are rewound and calandered together at a time to produce a two ply roll that further undergoes converting into finished product.

By utilizing the process described above and the substrate or finishings described above, one embodiment of the invention illustrated that the optimum addition of DC8600 was found to be approximately 0.5% (i.e. 5 kg DC8600 per 1000 kg or 1 Tonne) by weight of air dry pulp fibers, where generally the best gain in handfeel (i.e. 7 to 8 wws units) was experienced in a sustainable process. The gain in handfeel relates to a perceived improvement by approximately 70% to 80% of a human group.

Furthermore it was observed that regardless of the added DC8600 it was preferable to include the calendering step to improve the surface feel aspect of softness of the LDC papers utilized. Otherwise without calendering the paper, any handfeel result was insignificantly different between the variants tested.

The range of basis weights for the treated paper, when machine dry after calendering can extend from 8 to 20 pounds per ream (ream defined as 3000 square feet of paper). Preferably the basis weight range for the pre-treated paper when machine dry after calendering is from 8 to 12 pounds per ream.

Moreover unlike most other paper softeners, where handfeel is improved but with a loss in tensile strength of the treated paper, it was observed that the treatment described herein substantially maintained the tensile strength in the machine dry paper web for additions to 10 kg DC8600 per Tonne air dried pulp fiber. There was also some evidence to show modest improvement in the tensile strength in the dry paper web including its wet tensile strength.

Generally speaking in the pulping process the pH is in the range of 5 to 9; more preferably 6 to 8, and still more preferably neutral. Typical temperatures of the water were used as known by people skilled in the art at around 33 to 80 degrees Fahrenheit. Furthermore typical Yankee temperatures were used.

Application of Microcapsules to Tissue Paper

1. Background

The following relates to the application of microcapsules to tissue paper in order to impart softness and/or scent to the sheet. When shear or excessive pressure is applied to the microcapsules (as may occur during wiping or blowing one's nose, etc.) the capsules are designed to break, releasing the softening oil and/or other liquids, into the sheet and unto the skin of fingers, etc.

2. Method

The microcapsules were applied by spraying suspensions of varying concentration onto a continuous moving roll of tissue paper. Dosage levels were controlled by varying the speed and spray flow rate. The apparatus used is shown in FIG. 12.

For example a 12"-wide roll of tissue was fed into an open nip formed by a top and bottom roll and moving belt. No nip pressure was applied and the top roll remained stationary. The tissue sheet was reeled onto the winder at the opposite end of the adhesion tester, after passing under a mist of microcapsule suspension sprayed by an atomizing nozzle.

Each targeted dosage consisted of one "run". The beginning and end of each run were indicated by tabs placed in the roll of tissue as it was being reeled. There were approximately 4-5 runs per winder roll, after which the roll was set aside and a new one started. The following day, samples from each individual run were manually re-wound on cardboard cores with the treated side of the tissue located on the inside of the rolls, as indicated by colored tape.

Figure 12:
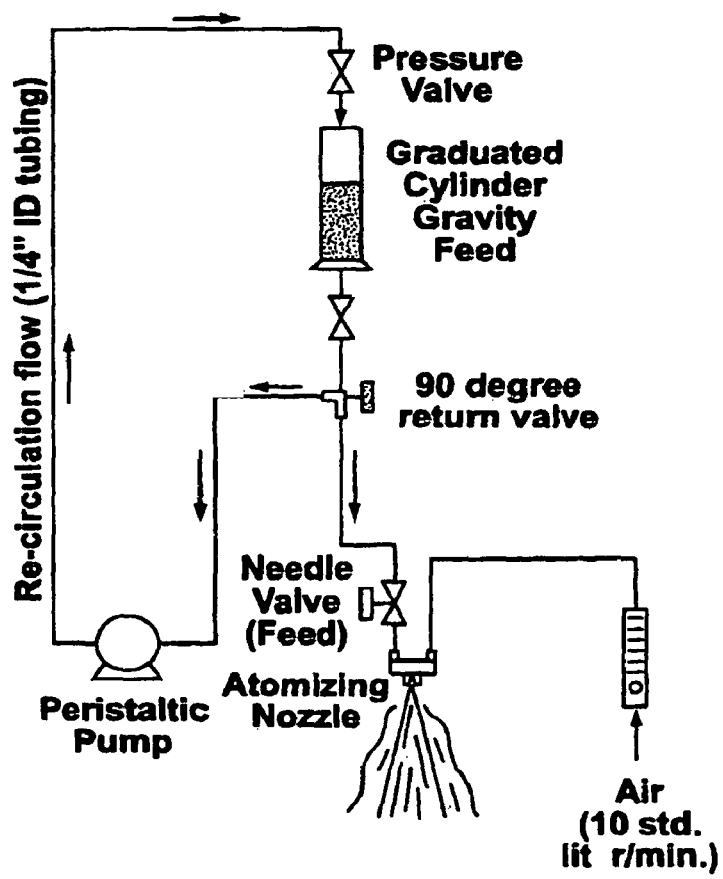
FIG. 12 is a detailed diagram of a spray system.

A detailed diagram of the spray system is shown in FIG. 12. The spray nozzle was a stainless steel atomizing nozzle with a #2050 fluid cap and a #62240-60 degree air cap supplied by Spray Engineering (Mississauga). Air was supplied to the nozzle at 10 standard litres per minute (L/min.) as measured by a rotameter. The liquid was fed by gravity using a graduated cylinder located several feet above the nozzle. The liquid flow rate into the nozzle was controlled by a Whitney SS-31 RF4 needle valve. The air and liquid connections to the nozzle were made with ¼" Swagelock.

Part of the flow to the nozzle valve was diverted and re-circulated back to the graduated cylinder with a Peristaltic pulp, using ⅜" OD, (¼" ID) Tygon tubing. This recirculation was necessary to keep the microcapsule suspension dispersed before entering the nozzle. A pressure valve (located just prior to the graduated cylinder) provided sufficient back pressure to maintain uniform flow rates.

Nozzle flow rates varied from 10-30 millilitres per minute (ML/min.), to target recommended microcapsule dosages of 0.019-0.37 g/m$^2$ (dry basis). These dosages were obtained by trial and error, by turning the combination of back pressure, feed valve and return valves. The flow rates were measured by stopwatch from the graduated cylinders.

3. Chemical Additives

Three solutions were used to prepare the recipes in this study namely:

Deionized Water (DIW)

3M Microcapsules (35 micron size, hard shell filled with mineral oil) @34.3% solids in solution.

Carboxymethylcellulose (CMC) (Kruger P-1202 by Amtex) @2% solids in solution.

To prevent spoilage, each of these solutions contained small amounts of sodium benzoate at ≈0.1% w/w.

Three recipes were used, and are listed below in Table I.

TABLE 1

RECIPES SPRAYED ONTO TISSUE

| RECIPE | | COMMENT | TOTAL SOLIDS (%) | ACTIVE MICROCAPS SOLIDS (%) |
|---|---|---|---|---|
| RECIPE #1 | 1 part of 34% Microcaps suspension, 10 parts of 2% CMC sol'n | Microcaps plus adhesive | 4.9% | 3.1% |
| RECIPE #2 | 100% DIW (Water only, control) | Water only (control) | n/a | n/a |
| RECIPE #3 | 1 part Microcaps suspension @ 34%, 10 parts DIW | Microcaps Only | 3.1% | 3.1% |

Estimating the Dosages

The applied dosages were estimated by assuming the tissue sheet picked up 100% of the liquid coming out of the nozzle:

$$\text{Wet Pickup (g/m}^2\text{)} = \frac{(FlowRate)(p)}{(\text{Speed})(\text{Width})}$$

$$\text{Dry Pickup (g/m}^2\text{)} = \text{Wet Pickup}(X_{Solids})$$

where:

$FlowRate$ = nozzle flow rate (mL/min.)

$p$ = liquid density, assumed to be that of water (1 g/ml).

Width 12 in (0.3048 m)

$X_{Solids}$ active solids content

Note that the mass as sodium benzoate in the recipes was assumed negligible

4. Results

Eighteen samples were prepared and manually re-wound on cardboard cores July 21. The results are summarized in Table II.

TABLE II

| Sample Label | Targeted Speed (m/min) | Actual Speed (m/min) | Nozzle Flow Rate (ML/min) | Microcaps Active Solids | CMC Active Solids | Total Solids | Estimated Total Pickup (gm/m²) | Estimated CMC Pickup (gm/m²) | Estimated Microcaps Pickup (gm/m²) | Estimated Water Pickup (gm/m²) | Comments |
|---|---|---|---|---|---|---|---|---|---|---|---|
| RECIPE #1. Microcaps/CMC Mixture | | | | | | | | | | | |
| | 20 | 19.9 | 10.4 | 3.1% | 1.8% | 4.9% | 1.72 | 0.03 | 0.05 | 1.64 | |
| | 30 | 29.2 | 10.7 | 3.1% | 1.8% | 4.9% | 1.20 | 0.02 | 0.04 | 1.14 | |
| | 50 | 45.9 | 10.3 | 3.1% | 1.8% | 4.9% | 0.74 | 0.01 | 0.02 | 0.70 | |
| | 80 | 79.8 | 10.0 | 3.1% | 1.8% | 4.9% | 0.41 | 0.01 | 0.01 | 0.39 | |
| | 10 | 9.6 | 9.8 | 3.1% | 1.8% | 4.9% | 3.33 | 0.06 | 0.10 | 3.17 | |
| RECIPE #2. Control (Water Only) | | | | | | | | | | | |
| | 10 | 10.0 | 8.9 | 0.0% | 0.0% | 0.0% | 2.91 | 0.00 | 0.00 | 2.91 | Pulsing spray when water is used |
| | 2 | 19.9 | 9.7 | 0.0% | 0.0% | 0.0% | 1.59 | 0.00 | 0.00 | 1.59 | Pulsing spray when water is used |
| | 30 | 29.0 | 9.4 | 0.0% | 0.0% | 0.0% | 1.06 | 0.00 | 0.00 | 1.06 | Pulsing spray when water is used |
| | 50 | 49.7 | 9.4 | 0.0% | 0.0% | 0.0% | 0.62 | 0.00 | 0.00 | 0.62 | Pulsing spray when water is used |
| | 8 | 80.4 | 9.0 | 0.0% | 0.0% | 0.0% | 0.37 | 0.00 | 0.00 | 0.37 | Pulsing spray when water is used |
| | | | | | | | n/a | n/a | n/a | n/a | Control. Sheet passing thru, no spray. |
| RECIPE #3. Water/Microcaps Mixture | | | | | | | | | | | |
| | 50 | 50.3 | 29.3 | 3.1% | 0.0% | 3.1% | 1.91 | 0.00 | 0.06 | 1.85 | |
| | 75 | 74.2 | 30.8 | 3.1% | 0.0% | 3.1% | 1.36 | 0.00 | 0.04 | 1.32 | |
| | 100 | 100.6 | 34.3 | 3.1% | 0.0% | 3.1% | 1.12 | 0.00 | 0.03 | 1.08 | |
| | 125 | 122.2 | 27.3 | 3.1% | 0.0% | 3.1% | 0.73 | 0.00 | 0.02 | 0.71 | |
| | 50 | 51.5 | 29.3 | 3.1% | 0.0% | 3.1% | 1.86 | 0.00 | 0.06 | 1.81 | |
| | 10 | 10.2 | 29.3 | 3.1% | 0.0% | 3.1% | 9.44 | 0.00 | 0.29 | 9.14 | Over-dosing the sheet on purpose. |
| | 20 | 19.8 | 28.6 | 3.1% | 0.0% | 3.1% | 4.72 | 0.00 | 0.15 | 4.58 | Over-dosing the sheet on purpose. |

The results summarized in Table II point to the use of water to modify the paper by adding microcapsules containing valuable oily liquids such as fragrance or the like. These applications are useful, but depending on the water added such water will tend to deteriorate the property of the web and therefore must be carefully controlled.

Another embodiment of the invention resides in substituting the water with room temperature non-volatile non-aqueous liquids such as mineral oil based lotions or polyethylene glycol based lotions as illustrated in FIGS. 15 and 16.

As can be seen from FIGS. 15 and 16 by utilizing ratios of approximately 4 to 10 parts carrier to one part fragrance, the fragrance will tend to stay longer with the carrier and in a sense the fragrance is bound to the cellulostic fibers by the lotion sprayed thereon.

In particular one can see from FIG. 15 the carrier liquids used therein comprise food grade mineral oil designated for example for FGWO35 sold as "Purity" brand by Petro-Canada. The reference 35 generally relates to the viscosity as 35 centistokes.

The fragrance type and the add on by wt/wt percent is also shown in FIG. 15. The reference to lipocaps relates to the trade name for microcapsules from Lipo Technologies, whereas other fragranced and coloured microcapsules were prepared by 3M. As can be seen from FIG. 15 by utilizing the carriers described therein the invention is not restricted to microcapsules but can include fragrances or aromas as well as microcapsules of same.

FIG. 16 also refers to a Paraflex HT-68 which is another example of a mineral oil from Petro Canada. Moreover FIG. 16 includes other examples of carrier liquid compositions and surfactants as well as fragrance types. For example MEG relates to a mixture of menthol, eucalyptus and camphor aromas as blended by Compagnie Parento Limited.

Moreover FIG. 16 illustrates the application of the carrier and fragrance by means of flexographic press and includes specifications of an example of anilox roll, plate roll and nip gap. However, such specifications are for illustrative purposes only and should not be limited thereto. Furthermore the carrier fragrance may also be applied by spraying or rotogravure press.

FIG. 17 illustrates the use of a surfactant such as DC 8600 which is added to enhance the tactile feel of the web being printed or sprayed in a manner described above.

More specifically the DC 8600 may be included as part of the lotion to improve the tactile characteristics of the facial tissue. Since the DC 8600 may have a trace fragrance itself, the carrier system described in FIG. 17 may be utilized to improve the fragrance of the final product.

FIG. 17 also illustrates that in one embodiment of the invention the carrier and surfactant along with the fragrance and other ingredients such as aloe and vitamin E can be applied to a web of cellulostic fiber by flexographic means. By utilizing a composition of approximately:
  less than 1% by weight of aloe
  less than 1% by weight of vitamin E
  less than 1% by weight of fragrance
  60% DC 8600
  remainder mineral oil
and applying same to a facial tissue, it was observed that the trace substances tended to "stay" with the facial tissues and good tactile feel was exhibited with the use of the DC 8600 as described above.

FIG. 18 illustrates specific results observed utilizing the method described in FIG. 17.

Various embodiments of the invention have now been described in detail. Since changes in and/or additions to the above-described best mode may be made without departing from the nature, spirit or scope of the invention, the invention is not to be limited to said details.

We claim:

1. A tissue paper product comprising a web of non-woven wood pulp fibers to which is applied an essentially anhydrous composition comprising approximately by weight less than 1% of aloe;
   less than 1% of vitamin E;
   about 60%-99% of a hydrophilic softener composition comprising by weight Bis ($C_{13}$-$C_{15}$ Alkoxy) PG Amodimethicone (and) PEG/PPG-24/24 Methyl Ether Glycidoxy Dimethicone; and
   the remainder mineral oil; wherein said paper is imparted with an increase in softness without loss of wet tensile strength as compared with said paper without said application.

2. A tissue paper product according to claim 1, wherein said web comprises approximately: (i) 55% by weight as bleached eucalyptus pulp and (ii) 45% by weight as bleached northern softwood kraft pulp.

3. A tissue paper product according to claim 1, further comprising a carrier containing an additive selected from the group consisting of fragrance, vitamin E and its derivatives, aloe, a colouring agent and combinations thereof.

4. A tissue paper product according to claim 3, including a fragrance comprising one part of concentrated fragrance together with four to ten parts carrier.

5. A tissue paper product according to claim 3, wherein the carrier comprises microcapsules.

6. A tissue paper product according to claim 3, wherein the carrier for the additive is selected from the group consisting of food grade mineral oil and polyethylene glycol.

7. A tissue paper product according to claim 3, including a fragrance comprising aromatic chemicals and essential oils.

8. A tissue paper product according the claim 7, wherein the essential oil is selected from the group consisting of menthol, eucalyptus oil, camphor gum, vanilla and combinations thereof.

9. A tissue paper product according to claim 1, comprising a multiple ply sheet.

10. A method of preparing a tissue paper product as defined in claim 1, comprising applying the essentially anhydrous composition to said web using an application technique selected from the group consisting of spraying, flexographic printing and roto-gravure printing.

11. A method according to claim 10, wherein said composition is applied to at least one surface of said web.

* * * * *